(12) United States Patent
Yang et al.

(10) Patent No.: US 7,816,094 B2
(45) Date of Patent: Oct. 19, 2010

(54) METHOD FOR QUANTITATIVE ANALYSIS OF INTERACTIONS BETWEEN HIF-1ALPHA C-TERMINAL PEPTIDES AND CBP OR P300 PROTEINS AND METHOD OF SCREENING INHIBITORS USING THE SAME

(75) Inventors: Eun-Gyeong Yang, Seoul (KR); Dae-Ro Ahn, Seoul (KR); Hyun-Ju Cho, Sacheon-shi (KR)

(73) Assignee: Korea Institute of Science and Technology, Hawolgok-dong, Seongbuk-gu, Seoul (KR)

( * ) Notice: Subject to any disclaimer, the term of this patent is extended or adjusted under 35 U.S.C. 154(b) by 593 days.

(21) Appl. No.: 11/750,016

(22) Filed: May 17, 2007

(65) Prior Publication Data

US 2009/0029390 A1      Jan. 29, 2009

(30) Foreign Application Priority Data

Oct. 12, 2006   (KR) .................... 10-2006-0099389

(51) Int. Cl.
  *G01N 33/53*   (2006.01)
  *G01N 33/543*   (2006.01)
(52) U.S. Cl. .................... 435/7.21; 435/7.1; 436/501; 436/518; 422/50; 500/300; 500/350
(58) Field of Classification Search .................... None
   See application file for complete search history.

(56) References Cited

U.S. PATENT DOCUMENTS

2006/0172323 A1   8/2006   Livingston et al.

FOREIGN PATENT DOCUMENTS

| JP | 10-287870 | 10/1998 |
| JP | 2003-501061 | 1/2003 |
| JP | 2005-526515 | 9/2005 |

OTHER PUBLICATIONS

Freedman et al. (Proceedings of the National Academy of Sciences of the Untied States of America, Apr. 16, 2002, vol. 99, No. 8., pp. 5367-5372).*
Vleugel et al. (Human Pathology, Aug. 2006, vol. 37., No. 8, pp. 1085-1092).*
Burke et al. (Combinatorial Chemistry & high Throughput Screening, 2003 vol. 6, pp. 183-194).*
NCBI, AAC51770, CREB-binding protein, NCBI Sequence View web site, http://www.ncbi.nlm.nih.gov/, Sep. 29, 1997, pp. 1-3.
NCBI, XP001168473, Predicted: E1A binding protein p300 isoform 2 [Pan troglodytes], NCBI Sequence View web site, http://www.ncbi.nlm.nih.gov/, Sep. 16, 1996, pp. 1-3.

* cited by examiner

*Primary Examiner*—Lisa V Cook
(74) *Attorney, Agent, or Firm*—Lexyoume IP Group, PLLC.

(57) ABSTRACT

A method for quantitative analysis of interactions between fluorescein-labeled HIF-1α (alpha) C-terminal peptides and cAMP-responsive element binding protein (CBP) or p300 proteins, and a method of screening inhibitors against the formation of HIF-1α-p300 or HIF-1α-CBP protein complexes using the above method is described.

13 Claims, 14 Drawing Sheets

SEQUENCE LISTING

<160> NUMBER OF SEQ ID NOS: 6

<210> SEQ ID NO 1
<211> LENGTH: 450
<212> TYPE: PRT
<213> ORGANISM: Artificial Sequence
<220> FEATURE:
<223> OTHER INFORMATION: Amino acid sequence for truncated CBP protein

<400> SEQUENCE: 1

```
Met Ala Glu Asn Leu Leu Asp Gly Pro Pro Asn Pro Lys Arg Ala Lys
 1               5                  10                  15

Leu Ser Ser Pro Gly Phe Ser Ala Asn Asp Ser Thr Asp Phe Gly Ser
                20                  25                  30

Leu Phe Asp Leu Glu Asn Asp Leu Pro Asp Glu Leu Ile Pro Asn Gly
            35                  40                  45

Gly Glu Leu Gly Leu Leu Asn Ser Gly Asn Leu Val Pro Asp Ala Ala
        50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190
```

```
Ser Gly His Ser Leu Ile Asn Gln Ala Ser Gln Gly Gln Ala Gln Val
            195                 200                 205

Met Asn Gly Ser Leu Gly Ala Ala Gly Arg Gly Arg Gly Ala Gly Met
        210                 215                 220

Pro Tyr Pro Thr Pro Ala Met Gln Gly Ala Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
        275                 280                 285

Gly Ala Thr Gly Val Asn Pro Gln Leu Ala Ser Lys Gln Ser Met Val
    290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
        355                 360                 365

Arg Arg Glu Gln Ala Asn Gly Glu Val Arg Ala Cys Ser Leu Pro His
370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
                405                 410                 415

Ser His Trp Lys Asn Cys Thr Arg His Asp Cys Pro Val Cys Leu Pro
            420                 425                 430

Leu Lys Asn Ala Ser Asp Lys Arg Asn Gln Gln Thr Ile Leu Gly Ser
        435                 440                 445

Pro Ala
    450

<210> SEQ ID NO 2
<211> LENGTH: 221
<212> TYPE: PRT
<213> ORGANISM: Artificial Sequence
<220> FEATURE:
<223> OTHER INFORMATION: Amino acid sequence for truncated p300 protein

<400> SEQUENCE: 2

Pro Asn Met Gly Gln Gln Pro Ala Pro Gln Val Gln Asn Pro Gly Leu
1               5                   10                  15

Val Thr Pro Val Ala Gln Gly Met Gly Ser Gly Ala His Thr Ala Asp
            20                  25                  30

Pro Glu Lys Arg Lys Leu Ile Gln Gln Gln Leu Val Leu Leu Leu His
        35                  40                  45

Ala His Lys Cys Gln Arg Arg Glu Gln Ala Asn Gly Glu Val Arg Gln
    50                  55                  60

Cys Asn Leu Pro His Cys Arg Thr Met Lys Asn Val Leu Asn His Met
65                  70                  75                  80

Thr His Cys Gln Ser Gly Lys Ser Cys Gln Val Ala His Cys Ala Ser
                85                  90                  95
```

```
Ser Arg Gln Ile Ile Ser His Trp Lys Asn Cys Thr Arg His Asp Cys
            100                 105                 110

Pro Val Cys Leu Pro Leu Lys Asn Ala Gly Asp Lys Arg Asn Gln Gln
        115                 120                 125

Pro Ile Leu Thr Gly Ala Pro Val Gly Leu Gly Asn Pro Ser Ser Leu
    130                 135                 140

Gly Val Gly Gln Gln Ser Ala Pro Asn Leu Ser Thr Val Ser Gln Ile
145                 150                 155                 160

Asp Pro Ser Ser Ile Glu Arg Ala Tyr Ala Ala Leu Gly Leu Pro Tyr
                165                 170                 175

Gln Val Asn Gln Met Pro Thr Gln Pro Gln Val Gln Ala Lys Asn Gln
            180                 185                 190

Gln Asn Gln Gln Pro Gly Gln Ser Pro Gln Gly Met Arg Pro Met Ser
        195                 200                 205

Asn Met Ser Ala Ser Pro Met Gly Val Asn Gly Val
    210                 215                 220

<210> SEQ ID NO 3
<211> LENGTH: 51
<212> TYPE: PRT
<213> ORGANISM: Artificial Sequence
<220> FEATURE:
<223> OTHER INFORMATION: Amino acid sequence for HIF-1a(776-826)

<400> SEQUENCE: 3

Ser Asp Leu Ala Cys Arg Leu Leu Gly Gln Ser Met Asp Glu Ser Gly
  1               5                  10                  15

Leu Pro Gln Leu Thr Ser Tyr Asp Cys Glu Val Asn Ala Pro Ile Gln
             20                  25                  30

Gly Ser Arg Asn Leu Leu Gln Gly Glu Glu Leu Leu Arg Ala Leu Asp
         35                  40                  45

Gln Val Asn
     50

<210> SEQ ID NO 4
<211> LENGTH: 41
<212> TYPE: PRT
<213> ORGANISM: Artificial Sequence
<220> FEATURE:
<223> OTHER INFORMATION: Amino acid sequence for HIF-1a(786-826)

<400> SEQUENCE: 4

Ser Met Asp Glu Ser Gly Leu Pro Gln Leu Thr Ser Tyr Asp Cys Glu
  1               5                  10                  15

Val Asn Ala Pro Ile Gln Gly Ser Arg Asn Leu Leu Gln Gly Glu Glu
             20                  25                  30

Leu Leu Arg Ala Leu Asp Gln Val Asn
         35                  40

<210> SEQ ID NO 5
<211> LENGTH: 39
<212> TYPE: PRT
<213> ORGANISM: Artificial Sequence
<220> FEATURE:
<223> OTHER INFORMATION: Amino acid sequence for HIF-1a(776-814)

<400> SEQUENCE: 5

Ser Asp Leu Ala Cys Arg Leu Leu Gly Gln Ser Met Asp Glu Ser Gly
  1               5                  10                  15
```

-continued

```
Leu Pro Gln Leu Thr Ser Tyr Asp Cys Glu Val Asn Ala Pro Ile Gln
            20                  25                  30

Gly Ser Arg Asn Leu Leu Gln
            35

<210> SEQ ID NO 6
<211> LENGTH: 35
<212> TYPE: PRT
<213> ORGANISM: Artificial Sequence
<220> FEATURE:
<223> OTHER INFORMATION: Amino acid sequence for HIF-1a(788-814)

<400> SEQUENCE: 6

Asp Glu Ser Gly Leu Pro Gln Leu Thr Ser Tyr Asp Cys Glu Val Asn
  1               5                  10                  15

Ala Pro Ile Gln Gly Ser Arg Asn Leu Leu Gln Gly Glu Glu Leu Leu
            20                  25                  30

Arg Ala Leu
            35
```

METHOD FOR QUANTITATIVE ANALYSIS OF INTERACTIONS BETWEEN HIF-1ALPHA C-TERMINAL PEPTIDES AND CBP OR P300 PROTEINS AND METHOD OF SCREENING INHIBITORS USING THE SAME

CROSS-REFERENCE TO RELATED APPLICATION

This application claims priority to and the benefit of Korean Patent Application No. 10-2006-0099389 filed in the Korean Intellectual Property Office on Oct. 12, 2006, the entire content of which is incorporated herein by reference.

BACKGROUND OF THE INVENTION (a) Field of the Invention

The present invention relates to a method for quantitative analysis of peptide interactions, more specifically to an interaction between fluorescein-labeled HIF-1α (alpha) C-terminal peptides and cAMP-responsive element binding protein (CBP) or p300 protein, and a method of screening inhibitors against interactions between HIF-1α peptides and CBP or p300 using the above method, namely a fluorescence polarization (FP)-based binding assay.

(b) Description of the Related Art

It is essential for existence that mammalian cells possess the ability to sense and respond to changes in oxygen levels, and this ability plays an important role in development and physiological processes as well as in human diseases such as angiogenesis, myocardial ischemia, cerebral ischemia, pulmonary hypertension, and various types of cancer. The responses to decreased oxygen level (hypoxia) are mediated by the master transcription factor, HIF-1 (hypoxia inducible factor-1).

HIF-1 (hypoxia inducible factor-1) is composed of α and β subunits, wherein the β subunit is always stably expressed, but HIF-1α (α subunit) is stabilized under a low oxygen condition (hypoxia), and degraded by proteosome under a normal oxygen condition (normoxia). Under hypoxia, the stabilized HIF-1α forms a protein complex that is combined by interactions between HIF-1α and transcription coactivators CBP (cAMP-response element-binding protein) or p300 in the nucleus, and subsequently activates transcription of target genes through binding with a hypoxia-response element (HRE) that exists at the promoter of target genes (Lando, D., et al., Genes. Dev., 16: 1466-14, 2002).

Because these CBP and p300 coactivators control the expression of the specific genes that are correlated with cell growth, differentiation, and homeostasis maintenance through operating in the end point of various signal transductions, controlling interactions between HIF-1α and CPB or p300 proteins is useful for not only treatment of ischemic diseases as to coronary insufficiency, brain ischemia, and blood ischemia, but also for research of cancer therapy involved with inhibiting blood vessel formation.

The CBP or p300 protein has a cysteine-/histidine-rich 1(CH1) domain containing $Zn^{2+}$ binding factor, wherein the CH1 domain interacts with the C-terminal transactivation domain (C-TAD) of HIF-1α (Kung, A. L., et al., Nature Medicine, 6: 1335-1340, 2000). Also, it has been known that each of complex structures formed by interactions between 331-418th amino acid regions of p300 protein and 792-824th amino acid peptides of HIF-1α, and between 345-439th amino acid regions of CBP protein and 776-826th amino acid peptides of HIF-1α, were revealed by NMR research (Dames, S. A., et al., PNAS, 99: 5271-5276, 2002). It can be determined from these complex structures that the CH1 is stabilized by various hydrophobic and ionic interactions, because it is operating as a scaffold for the folding of the C-terminal domain of HIF-1α. Also, unlike NMR analysis which uses peptides at a high concentration of several mM, the present invention exploited a binding analysis that uses the amino acid regions of HIF-1α that are able to sufficiently bind even at low concentration of µM units.

The expression of HIF-1 dependent target genes is controlled by two different oxygen-dependent mechanisms, proline hydroxylation and asparagine hydroxylation. The hydroxylation of proline residues in the ODD (oxygen-dependent domain) of HIF-1α by HIF-1α-specific prolyl hydoryxlases induces HIF-1α destruction, but the hydroxylation of asparagines diminishes the expression of HIF-1 dependent target genes by inactivating the interaction between the C-TAD of HIF-1α and CBP or p300.

Initially, FIH-1 (Factor-inhibiting HIF-1) protein (Mahon, P. C., et al., Genes Dev., 15: 2675-2686, 2001) was known to hinder HIF-1; however, it was revealed thereafter that it has an oxygen sensor feature that participates in the control of HIF-1α (Lando, D., et al., Gene Dev., 16: 1466-1471, 2002). Namely, the FIH-1 belongs to 2-oxoglutarate and iron-dependent dioxygenase protein (Safran, M., et al., J. Clin. Invest., 111: 779-783, 2003), and hydroxylates Asn-803 in the C-TAD of HIF-1α, thereby disrupting the interaction of HIF-1α with CBP or p300 and blocking the HIF-mediated transactivation (Lando, D., et al., Science, 295: 858-861, 2002).

In addition to asparagine hydroxylation for the transcriptional activity of HIF-1α toward target genes, posttranslational modifications of other residues in C-TAD have been proposed to influence the fine-turning of HIF-1α function (Brahimi-Horn., et al., Cell, Signal., 17: 1-9, 2005). One of representative mechanisms for HIF-1α transcriptional activity control is phosphorylation of transcriptional factors (Holmberg, C. I., et al., Trends Biochem. Sci., 27: 619-627, 2002), namely direct phosphorylation of HIF-1α under normoxia and hypoxia has been reported (Brahimi-Horn, C., et al., Cellular Signaling, 17: 1-9, 2005).

Phosphorylation of HIF-1α can also modulate its transcriptional activity. The activation of mitogen-activated protein kinase (MAPK) induced by hypoxia has been suggested to phosphorylate HIF-1α, which appears to increase the interaction between HIF-1α and p300 protein, but is not correlated with its transcriptional activity (Sang, N., et al., J. Biol. Chem., 278: 14013-14019, 2003). However, the phosphorylation sites responsible for nuclear accumulation of HIF-1α have been identified to reside far from the C-TAD (Mylonis, I., et al., J. Biol. Chem., 281: 33095-33106, 2006). On the other hand, Thr-796 in C-TAD has been indicated as a candidate for phosphorylation possibly by casein kinase 2 (CK2) (Mottet, D., et al., Int. J. Cancer, 117: 764-774, 2005). Despite the abundance of data indicating transcription activity affected by posttranslational modifications of the C-TAD of HIF-1α, disputable information is also available for the direct effects of such modifications on the binding between HIF-1α C-TAD and p300 or CBP proteins.

In addition, it has been reported that NO (nitric oxide) increases or decreases the stability of HIF-1α depending on the cell type and NO concentration (Bilton, R. L., et al., Eur. J. Biochem., 270: 791-798, 2003). In addition, S-nitrosylation of Cys-800 of HIF-1α has been reported to increase HIF-1α transcriptional activity possibly by enhancing its p300 binding (Yasinska, I. M., et al., FEBS Lett., 549: 105-109, 2003), but some conflicting results have also been reported (Brahimi-Horn, C., et al., Cell, Signal., 17: 1-9, 2005).

Until now, various biochemical or immunological methods have been used for analysis of interactions between HIF-1α and CBP or p300. First of all, a two-hybrid assay has been used as a method that measures interactions between HIF-1α and CBP or p300, and in more detail, a method for measuring the transcriptional activity by binding of two proteins, wherein the proteins were manufactured by fusing DNA binding domain (DBD) of yeast GAL4 transcription factor with CBP or p300, and its transcriptional activation domain (TAD) with HIF-1α, respectively.

In another method, one protein among HIF-1α and CBP or p300 is labeled with easily detectable material and the other protein is fixed in the solid support, and then the interaction of the two proteins is measured.

Another method is based on coimmunoprecipitates using the antibody that recognizes the specific region of HIF-1α to identify CBP or p300 and HIF-1α binding. However, these methods have many shortcomings in that massive reagents are demanded, that the process is complicated, that the test time is long, and that a radioactive isotope must be used.

Additionally, there is an indirect method, namely a reporter assay that reveals the transcriptional activity by the interaction between HIF-1α and hypoxia response element (HRE) on target genes after HIF-1α binding to CBP or p300 proteins. One example is a method using the Epo-Luciferase (Kung, A. L., et al., Nature Medicine, 6: 1355-1340, 2000).

Therefore, a simpler measuring method for quantitative analysis of the interactions between HIF-1α and CBP or p300 has been in demand, because the biochemical, immunological, or radioactive isotope-labeling methods as described above have many shortcomings in that massive reagents are demanded, that the process is complicated, that the test time is long, and that the radioactive isotope must be used.

As a result, an analyzing method using 96-well plates that is able to observe interactions between HIF-1α and CBP or p300 in a relatively short time without use of radioactive materials was developed (Kung, A. L., et al., Cancer Cell, 6: 33-43, 2004). This method is useful for screening chemical compounds inhibiting interactions between HIF-1α and CBP or p300, but has shortcomings of the requirement of using a plate coated with expensive avidin, europium-fused anti-GST antibody, and time-resolved fluorescence spectrometer.

SUMMARY OF THE INVENTION

The present inventors developed a method for quantitative analysis of the formation of a protein complex between fluorescein-labeled HIF-1α C-terminal peptides and CBP or p300 proteins, by measuring the change of fluorescence polarization (FP) values.

The present inventors also found that the method was useful for examining direct effects of posttranslational modifications (hydroxylation, S-nitrosylation, and phosphorylation) of HIF-1α C-TAD (C-terminal transactivation domain), or possibly for screening inhibitors against the formation of HIF-1α-CBP or HIF-1α-p300 protein complexes.

An object of the present invention is to provide a simple method for quantitative analysis of interactions between HIF-1α C-terminal peptides and CBP or p300 proteins.

Another object of the present invention is to provide a method of screening inhibitors against interactions between HIF-1α C-terminal peptides and CBP or p300 proteins using the above method.

Yet another object of the present invention is to provide modified fluorescein-labeled HIF-1α C-terminal peptides including at least 41-51 amino acids on the amino acid sequences of the HIF-1α C-terminal region responsible for interaction with CBP or p300 proteins.

To achieve these objects, the present invention provides a method for quantitative analysis of interactions between fluorescein-labeled HIF-1α C-terminal peptides and CBP or p300 proteins.

In another aspect, the present invention provides a method of screening inhibitors against interactions between HIF-1α C-terminal peptides and CBP or p300 proteins using the above method, namely a fluorescence polarization (FP)-based binding assay.

In a further aspect, the present invention provides synthesized HIF-1α C-terminal peptides including at least 41-51 amino acids on the amino acid sequences of HIF-1α C-terminal responsible for interaction with CBP or p300 proteins, more preferably including 776-826 and 786-826 residues of the HIF-1α peptides denoted as F-HIF-1α-(776-826, SEQ ID NO: 3) and F-HIF-1α-(786-826, SEQ ID NO: 4), respectively.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing.

5A indicates the level of phosphorylation of F-HIF-1α (786-826, SEQ ID NO: 4) peptide reacting with normoxic (N) or hypoxic (H) kinase fractions.

DETAILED DESCRIPTION OF THE PREFERRED EMBODIMENTS

Figure 1A:
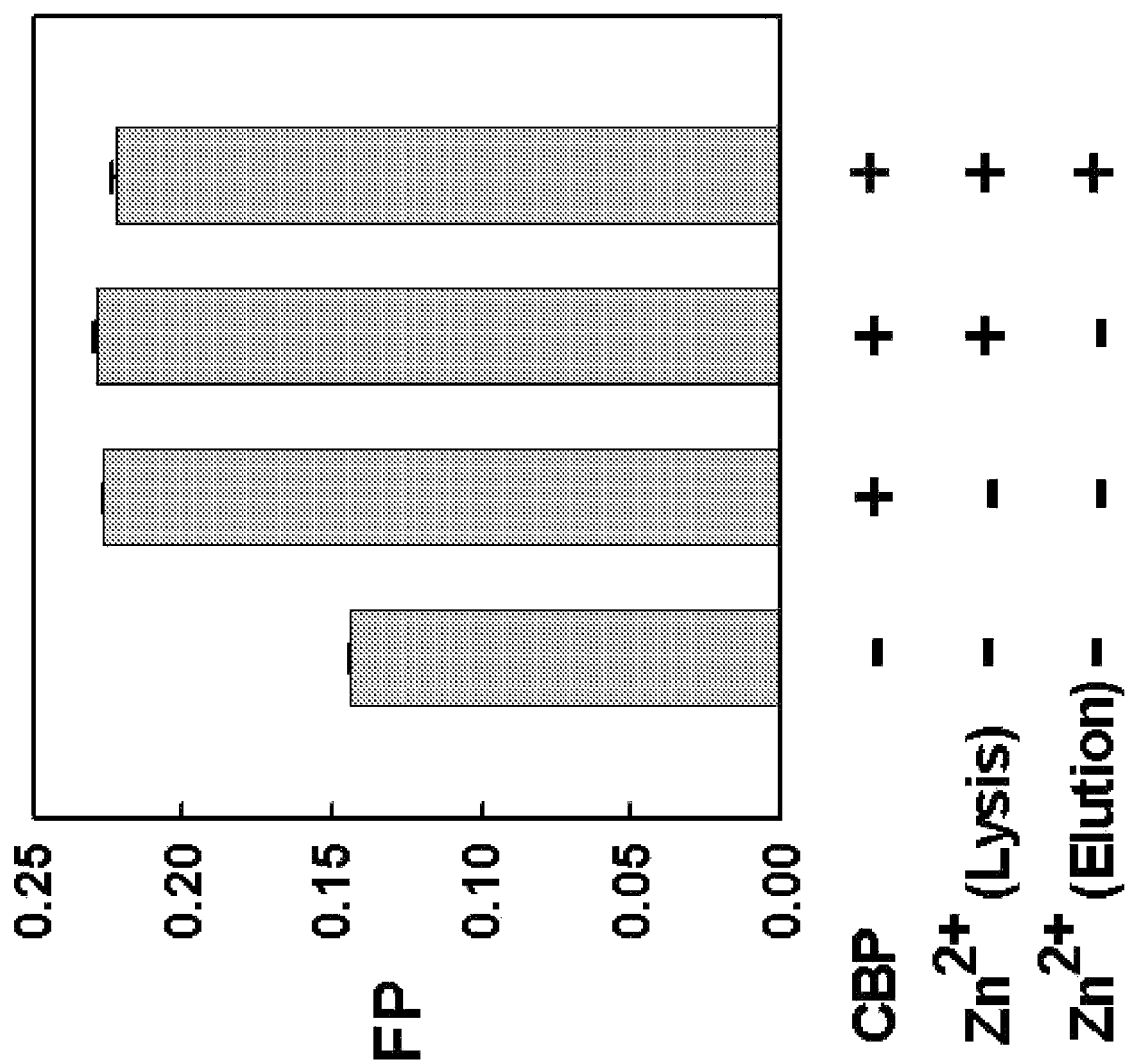
FIG. 1 is a graph showing the effects of $Zn^{2+}$ added in the preparation of CBP (FIG. 1A) or p300 (FIG. 1B) proteins on their interactions with fluorescein-labeled HIF-1α peptides, wherein peptides used in FIGS. 1A and 1B are to F-HIF-1α (776-826, SEQ ID NO: 3) and F-HIF-1α (786-826, SEQ ID NO: 4) peptides, respectively. Each point represents the average fluorescence polarization (FP) value of triplicate assays ±SD (standard deviation).

The present invention will now be explained in more detail.

The present invention provides a method for quantitative analysis of an interaction between HIF-1α and cAMP-responsive element binding protein (CBP) or p300 protein, including the steps of:

1) preparing a fluorescent probe by attaching a fluorescein to a peptide derived from the C-terminal transactivation domain (C-TAD) of HIF-1α protein;
2) reacting the fluorescent probe with CBP or p300 proteins; and
3) measuring fluorescence polarization (FP) values for the reaction mixture obtained in step 2) and then comparing with that of the fluorescent probe itself to analyze the changes of FP values.

In the quantitative analysis method, the fluorescent probe in step 1) can include:

a peptide having at least 41 amino acids which are consecutively present in the full-length amino acid sequence of HIF-1α (Accession No. AAA50152), wherein the peptide essentially contains the amino acid sequence through the $786^{th}$ amino acid to the $826^{th}$ amino acid in HIF-1α, as shown in SEQ ID NO: 4;

an aminocaproic acid linker conjugated to the N-terminus of the peptide; and a fluorophore linked at the end of aminocaproic acid.

Because if the peptide in the fluorescent probe is shorter than 41 amino acids, its binding activity for CBP or p300 is completely blocked, the peptide may have 41 or more amino acids consecutively present in the full-length amino acid sequence of HIF-1α. Further, because if the peptide is longer than 55 amino acids, its binding activity for CBP or p300 cannot be measured by fluorescence polarization changes due to the large fluorescence polarization value of the peptide, the peptide preferably has 41 to 55 consecutive amino acids in the full-length amino acid sequence of HIF-1α, more preferably 51 amino acids having the amino acid sequence of SEQ ID NO: 3, and even more preferably 41 amino acids having the amino acid sequence of SEQ ID NO: 4.

Also, the probe can include the amino acid sequences shown in SEQ ID NO: 3 on the amino acid sequences of HIF-1α, wherein the N-terminus of the peptide is conjugated with an aminocaproic acid linker, and the end of the linker is labeled with a fluorescein.

Also, the fluorescent probe in step 1) is not particularly limited, but additionally it is preferred that the fluorescent probe is connected with an aminocaproic acid linker at the N-terminus of the peptide, and labeled with a fluorescein, preferably FITC (fluorescein isothiocyanate), at the end of the linker as shown in SEQ ID NO: 3 or SEQ ID NO: 4 (Table 1).

In the above quantitative analysis method, the linker is not specifically limited, as long as it can be connected with the peptides irrespective of the kind of linker or without the linker, that is, it should be possible to minimize unnecessary changes of fluorescence intensity induced by interactions between fluorescein-labeled HIF-1α C-terminal peptides, namely a fluorescent probe and objective proteins, and can be used for FP measurement.

Also, the fluorophore may includes fluorescein, and the like, but not be limited thereto. For example, the fluorophore may be preferably selected from the group consisting of fluorescein isothiocyanate (FITC), phycoerythrin (PE), Texas Red (TR) and tetrame-thylrhodamine isothiocyanate (TRITC), fluorescein carboxylic acid (FCA), fluorescein thiourea (FTH), 7-acethocycoumarin-3-1, fluorescein-5-1, fluorescein-6-1, 2',7'-dichlorofluorescein-5-1, dehydrotetramethylosamine-4-1, tetramethylrhodamine-5-1, and tetramethylrhodamine-6-1, and more preferably, fluorescein isothiocyanate (FITC).

In the quantitative analysis method, the CBP or p300 proteins are not particularly limited, wherein the CBP protein preferably contains 1-450 amino acid sequences shown in SEQ ID NO: 1, and the p300 protein preferably contains 1-221 amino acid sequences shown in SEQ ID NO: 2. Further, the CBP or p300 proteins can include partial or full-length amino acid sequences including HIF-1α-binding sites on gene represented by GenBank Accession Number U85962 (CBP coding sequences) and U01877 (p300 coding sequences), respectively.

Preferred specific embodiment(s) of the present invention can provide synthesized CBP or p300 proteins, wherein the proteins can be isolated and purified from the cultured cells or medium. The method is not particularly limited, and more preferably the method for isolation and purification of the proteins can be selected from the group consisting of a method of separation of a protein based on the difference of molecular weight such as dialysis, ultra-filtration, gel-filtration, and SDS-PAGE, a method of separation of a protein based on a difference of electrical charge such as ion-exchange chromatography, and a method of separation of a protein based on a difference of hydrophilicity such as reverse-phase high performance liquid chromatography (RP-HPLC).

Also, the reaction in step 2) can be preferably induced by mixing of a fluorescent probe and CBP or p300 proteins within ranges from 1:1 (100 nM: 100 nM) to 1:30 (100 nM: 3000 nM), and more preferably within ranges from 1:2 (100 nM: 200 nM) to 1:10 (100 nM: 1000 nM).

In the quantitative analysis method, the FP measurement in step 3) is not particularly limited, and it is preferable to use a fluorescence spectrometer or a well plate-based fluorescence detector (Victor plate reader) for the FP measurement, wherein the change of FP values can be denoted by subtracting FP values of the fluorescent probe itself from FP values of the reactant measured in step 2). Herein, the fluorescent probe has a relatively small FP value as its molecular weight is very small. However, if the fluorescent HIF-1α peptide probes bind to CBP or p300 proteins having a large molecular weight, then the FP value of HIF-1α-CBP or HIF-1α-p300 complexes increases remarkably.

Consequently, it is possible to analyze whether HIF-1α binding to CBP or p300 proteins has occurred or not by determining the change of FP values measured before and after mixing of the fluorescent probe and CBP or p300 proteins. In more detail, from the change of FP values, it is possible to determine, for example, whether the complex is formed when the difference of the FP values is positive (+).

In addition, the present invention provides a method of screening inhibitors against an interaction between HIF-1α and CBP or p300 proteins, including the steps of:

1) adding an inhibitor candidate to a reaction solution containing a fluorescent probe and CBP or p300 protein, wherein the fluorescent probe is prepared by attaching a fluorescein to a peptide derived from C-terminal transactivation domain (C-TAD) of HIF-1α protein;
2) measuring the change of fluorescence polarization (FP) values of the reaction solution before and after addition of the inhibitor candidate; and
3) determining the candidate as an inhibitor by detecting the decrease of FP values of the reaction solution after addition of the inhibitor candidate.

In the screening method, the fluorescent probe in step 1) can include:

a peptide having at least 41 amino acids which are consecutively present in the full-length amino acid sequence of HIF-1α (Accession No. AAA50152), wherein the peptide essentially contains the amino acid sequence through the $786^{th}$ amino acid to the $826^{th}$ amino acid in HIF-1α, as shown in SEQ ID NO: 4;

an aminocaproic acid linker conjugated to the N-terminus of the peptide; and a fluorophore linked at the end of aminocaproic acid.

Because if the peptide in the fluorescent probe is shorter than 41 amino acids, its binding activity for CBP or p300 is completely blocked, the peptide may have 41 or more amino acids consecutively present in the full-length amino acid sequence of HIF-1α. Further, because if the peptide is longer than 55 amino acids, its binding activity for CBP or p300 cannot be measured by fluorescence polarization changes due to the large fluorescence polarization value of the peptide, the peptide preferably has 41 to 55 consecutive amino acids in the full-length amino acid sequence of HIF-1α, more preferably 51 amino acids having the amino acid sequence of SEQ ID NO: 3, and even more preferably 41 amino acids having the amino acid sequence of SEQ ID NO: 4.

Also, the probe can include the amino acid sequences shown in SEQ ID NO: 3 on the amino acid sequences of HIF-1α, wherein the N-terminus of the peptide is conjugated with an aminocaproic acid linker, and the end of the linker is labeled with a fluorescein.

Also, the fluorescent probe in step 1) is not particularly limited, and it is additionally preferable that the fluorescent probe is connected with an aminocaproic acid linker at the N-terminus of the peptide and is labeled with a fluorescein, preferably FITC (fluorescein isothiocyanate), at the end of the linker as shown in SEQ ID NO: 3 or SEQ ID NO: 4 (Table 1).

In this method, the linker is not specifically limited as long as it can be connected to the peptides irrespective of the kind of linker or without the linker, that is, it should be possible to minimize unnecessary changes of fluorescence intensity induced by interactions between fluorescein-labeled HIF-1α C-terminal peptides, namely a fluorescent probe and objective proteins, and be used for FP measurement.

Also, the fluorophore may includes fluorescein, and the like, but not be limited thereto. For example, the fluorophore can be preferably selected from the group consisting of fluorescein isothiocyanate (FITC), phycoerythrin (PE), TEXAS RED (TR) and tetrame-thylrhodamine isothiocyanate (TRITC), fluorescein carboxylic acid (FCA), fluorescein thiourea (FTH), 7-acethocycoumarin-3-1, fluorescein-5-1, fluorescein-6-1, 2', 7'-dichlorofluorescein-5-1, dehydrotet-ramethylosamine-4-1, tetramethylrhodamine-5-1, and tetramethylrhodamine-6-1, and more preferably can be fluorescein isothiocyanate (FITC).

In the screening method, the CBP or p300 proteins are not particularly limited, wherein it is preferable that the CBP protein contains 1-450 amino acid sequences shown in SEQ ID NO: 1, and the p300 protein contains 1-221 amino acid sequences shown in SEQ ID NO: 2. Further, the CBP or p300 proteins can include partial or full-length amino acid sequences including HIF-1α-binding sites on genes represented by GenBank Accession Number U85962 (CBP coding sequences) and U01877 (p300 coding sequences), respectively.

Also, the inhibitor candidate in step 2) is not particularly limited, and the candidate can preferably be selected from the group consisting of antibodies, peptides, oligonucleotides, and natural and synthetic compounds, which competitively inhibit the interaction between the fluorescent probe and CBP or p300 proteins.

Further, the present invention provides the method for quantitative analysis including the steps of:

a) preparing a fluorescent probe by attaching a fluorescein to a peptide derived from a C-terminal transactivation domain of a HIF-1α protein, reacting the fluorescent probe with a CBP or p300 protein, and then measuring FP values thereof;
b) treating the fluorescent probe with an enzyme selected from the group consisting of Factor-inhibiting HIF-1 (FIH-1), S-Nitroso-N-acetylpenicillamine (SNAP), and casein kinase 2 (CK2), reacting the enzyme-treated probe with a CBP or p300 protein, and then measuring FP values thereof; and
c) comparing the FP values measured in step a) and step b) to analyze the effect of the posttranslational modifications of the C-terminal transactivation domain (C-TAD) of the HIF-1α on CBP or p300 binding.

Practical and presently preferred embodiments of the present invention are illustrative as shown in the following examples. However, it will be appreciated that those skilled in the art, on consideration of this disclosure, may make modifications and improvements within the spirit and scope of the present invention.

EXAMPLE 1

Expression and Purification of CBP and p300 Proteins

For the expression of CBP and p300 proteins, according to an embodiment of the present invention, the truncated human CBP (amino acids 1-450) including an amino acid sequence as shown in SEQ ID NO: 1 and the truncated p300 (amino acids 1-221) including an amino acid sequence as shown in SEQ ID NO: 2 were subcloned in pGEX-KG (GE Healthcare Life Sciences, USA) and pGEX-4T-1 (Amersham Biosciences, USA) vectors, respectively, and then transformed into *E. coli* BL21 (Novagen).

The transformed cells were cultured in Luria-Bertani (LB) broth medium containing 50 ug/ml of ampicillin until the optical density (0.D) reached 0.6 at 37° C., and they were induced by the addition of 0.5 mM IPTG (isopropyl-β-D-thiogalactopyranoside) for 15 hours at 18° C. After centrifugation, the cells were resuspended in 10 ml phosphate buffered saline (PBS, pH 7.4; 110 mM NaCl, 1 mM DTT) containing PMSF (phenylmethylsulfonyl fluoride) and lysozyme at the final concentrations of 0.2 mM and 1 mg/ml, respectively, and then were lysed at 4° C. The cell extracts were mixed with 2% TRITON X-100, placed in ice for 10 min, and centrifuged at 13,000 rpm for 30 min. The supernatant was mixed with 1 mM DTT, agitated using glutathione-SEPHAROSE (Amersham Biosciences, USA) for 2 hours at 4° C., then the reaction mixtures were mixed with 10 times the volume of PBS, and then the supernatant was removed by centrifugation for 5 min. This process was repeated continuously 3 times, the supernatant was removed by centrifugation, and then the treated SEPHAROSE beads were added to a Bio-Spin® Disposable Chromatography column (Bio-Red). Then, unnecessary materials bound non-specifically to the beads were removed by filtering with 5 ml of PBS and 2 ml of 1 M NaCl.

Finally, GST-CBP and GST-p300 proteins were eluted from the beads using 10 mM of glutathione-Sepharose (Amersham Biosciences, USA), and then the purified fusion proteins were confirmed by SDS-PAGE and quantified by Bradford assay (Bio-Red).

EXAMPLE 2

Analysis of the Interaction Between Fluorescein-labeled HIF-1α Peptides and CBP or p300 Proteins 2-1. Synthesis of Fluorescein-Labeled HIF-1α Peptides Four fluorescein-labeled HIF-1α peptides containing the C-TAD of human HIF-1α were synthesized by conjugating FITC (fluorescein isothiocyanate) with the N-terminal insertion of an aminocaproic acid linker (Anygen, KwangJu, Korea), wherein the synthesized four peptides containing 776-826, 786-826, 776-814, and 788-822 amino acid residues were denoted as F-HIF-1α (776-826, SEQ ID NO: 3), F-HIF-1α (786-826, SEQ ID NO: 4), F-HIF-1α (776-814, SEQ ID NO: 5), and F-HIF-1α (788-822, SEQ ID NO: 6), respectively (Table 1).

by the formation of a protein-ligand complex through the interaction between the CBP or p300 proteins and the synthesized peptides that were manufactured by the method as described in above Example 1. The FP values were measured with a fluorescence spectrometer (Perkin-Elmer), which was set to have a slit width of 5 nm and a total integration time of 5 seconds. EBC Buffer (50 mM Tris and 120 mM NaCl; pH 8.0, 0.25% Nonidet P (NP)-40) was used for the binding reaction.

2-2. Analysis of the Interaction Between Fluorescein-Labeled HIF-1α Peptides and CBP or p300 Treated with or without $Zn^{2+}$ Because the cysteine-/histidine-rich 1(CH1) domain of CBP or p300 proteins that binds the C-terminal transactivation domain (C-TAD) of HIF-1α contains the $Zn^{2+}$-coordinating centers, an embodiment of the present invention first tested for the importance of $Zn^{2+}$ added in the preparation of CBP or p300 proteins by cell lysis and protein elution on their binding to the HIF-1α-derived peptides, wherein the GST-CBP or GST-p300 proteins containing the CH1 domain were prepared by cell lysis and protein elution in the presence or absence of $ZnSO_4$. 800 nM of CBP or p300 proteins in the EBC Buffer prepared from above Example 1 were mixed with 100 nM of F-HIF-1α(776-826, SEQ ID NO: 3) and F-HIF-1α(786-826, SEQ ID NO: 4) peptides at 25° C., respectively. Then, the FP (fluorescence polarization) values were measured.

The results indicated that the FP values significantly increased when the GST-CBP and GST-p300 were mixed with the peptides, wherein the FP values measured upon the formation of CBP-F-HIF-1α(776-826, SEQ ID NO: 3) and p300-HIF-1α(786-826, SEQ ID NO: 4) complex were higher

TABLE 1

Sequences of four fluorescein-labeled HIF-1α C-terminal peptides

| Synthesized peptides | Type |
|---|---|
| FITC-ACA-F-HIF-1α(776-826, SEQ ID NO: 3) | FITC-ACA-SDLACRLLGQSMDESGLPQLTSYDCEVNAPIQGSRNLLQGEELLRALDQVN |
| FITC-ACA-F-HIF-1α(786-826, SEQ ID NO: 4) | FITC-ACA-SMDESGLPQLLTSYDCEVNAPIQGSRNLLQGEELLRALDQVN |
| FITC-ACA-F-HIF-1α(776-814, SEQ ID NO: 5) | FITC-ACA-SDLACRLLGQSMDESGLPQLTSYDCEVNAPIQGSRNLLQ |
| FITC-ACA-F-HIF-1α(788-822, SEQ ID NO: 6) | FITC-ACA-DESGLPQLTSYDCEVNAPIQGSRNLLQGEELLRAL |

For generation of mutant peptides, single mutation products of the HIF-1α (786-826, SEQ ID NO: 4) prepared by PCR were also subcloned into pGEX-2T-1 (Amersham Biosciences, USA), and overexpressed in E. coli BL21 (DE3). After the GST fusion proteins were purified using glutathione-SEPHAROSE (Amersham Biosciences, USA), followed by GST removal with thrombin treatment, the resulting peptides were purified using reverse-phase HPLC and confirmed by MALDI-TOF mass spectrometry.

Figure 1B:
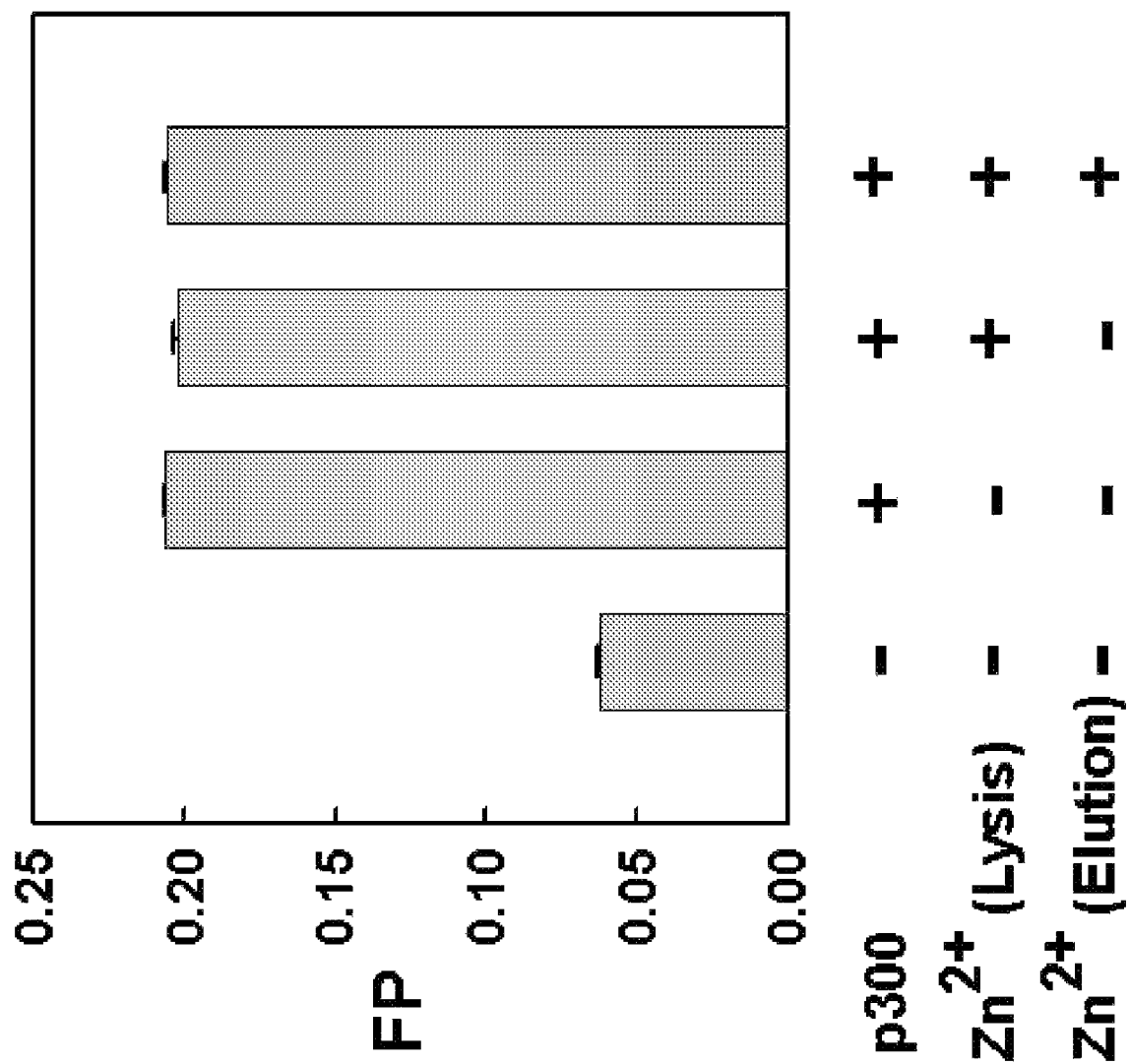

The binding affinity and features between the HIF-1α peptides and CBP or p300 proteins were analyzed by measuring the fluorescence polarization (FP) values that were changed than those for HIF-1α(776-826, SEQ ID NO: 3) and HIF-1α (786-826, SEQ ID NO: 4) peptides only, respectively (FIGS. 1A and 1B). However, there was no difference whether or not $ZnSO_4$ was added in the preparation of CBP or p300 proteins (FIGS. 1A and 1B), indicating that enough $Zn^{2+}$ is present in the bacterial culture media to form the complex of the HIF-1α peptides with the CH1 domain of GST-CBP or GST-p300 proteins.

Figure 2A:
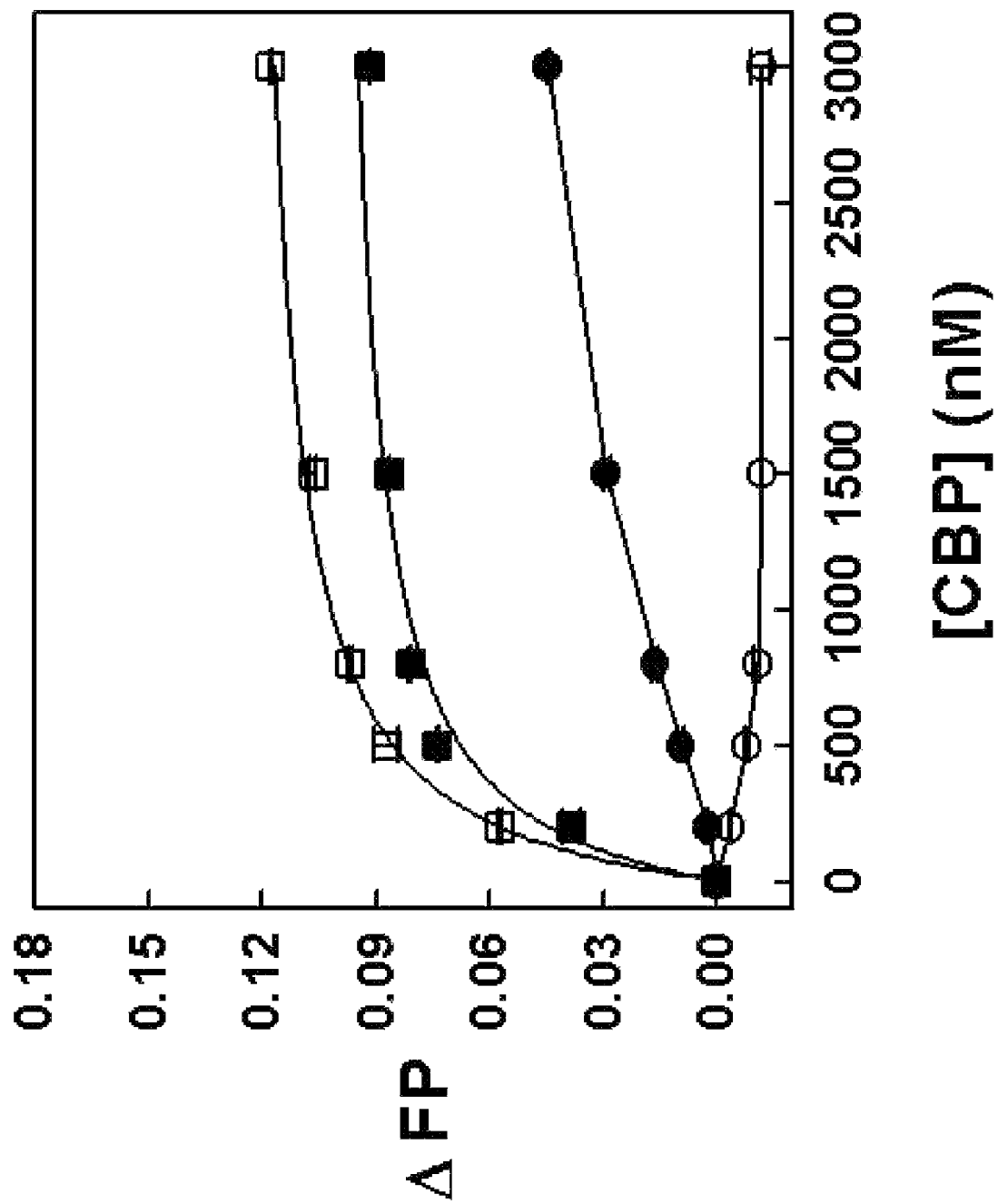
FIG. 2 is a graph showing the changes of FP values for four fluorescein-labeled HIF-1α peptides of various lengths binding to CBP (FIG. 2A) or p300 (FIG. 2B) proteins, wherein (■), (□), (●), and (○) indicate F-HIF-1α (776-826, SEQ ID NO: 3), F-HIF-1α (786-826, SEQ ID NO: 4), F-HIF-1α (788-822, SEQ ID NO: 6), and F-HIF-1α (776-814, SEQ ID NO: 5) peptides, respectively. Also, differences in FP (ΔFP) were determined by subtracting FP values of the fluorescein-labeled peptides in the absence of CBP or p300 proteins, and are presented.

2-3. Analysis of the Interaction Between Fluorescein-Labeled HIF-1α and CBP or p300 with Various Concentrations To compare interactions between the four peptides derived from different regions in HIF-1α C-TAD with CBP or p300, these fluorescein-labeled HIF-1α peptides were mixed with CBP proteins at varying concentrations from 0 to 3000 nM under the conditions of above Example 2-2, and then the FP (fluorescence polarization) values were measured (FIG. 2A). Because these peptides exhibited size-dependent basal FP values, net changes were calculated by subtracting FP values of the peptides alone from FP values of the protein complex.

In the case of CBP, FP values of HIF-1α(776-826, SEQ ID NO: 3) and HIF-1α(786-826, SEQ ID NO: 4) mixed with CBP increased with increasing GST-CBP concentrations, and eventually approached to plateaus, respectively (FIG. 2A). Also, the dissociation constants of these two peptides were determined to be 195.7 nM for HIF-1α(776-826, SEQ ID NO: 3) and 174.9 nM for HIF-1α(786-826, SEQ ID NO: 4), respectively. On the other hand, FP values of HIF-1α(788-822, SEQ ID NO: 6) increased much less than those of the above two peptides, and the values of HIF-1α(776-814, SEQ ID NO: 5) showed no increase up to 3000 nM of GST-CBP (FIG. 2A).

Figure 2B:
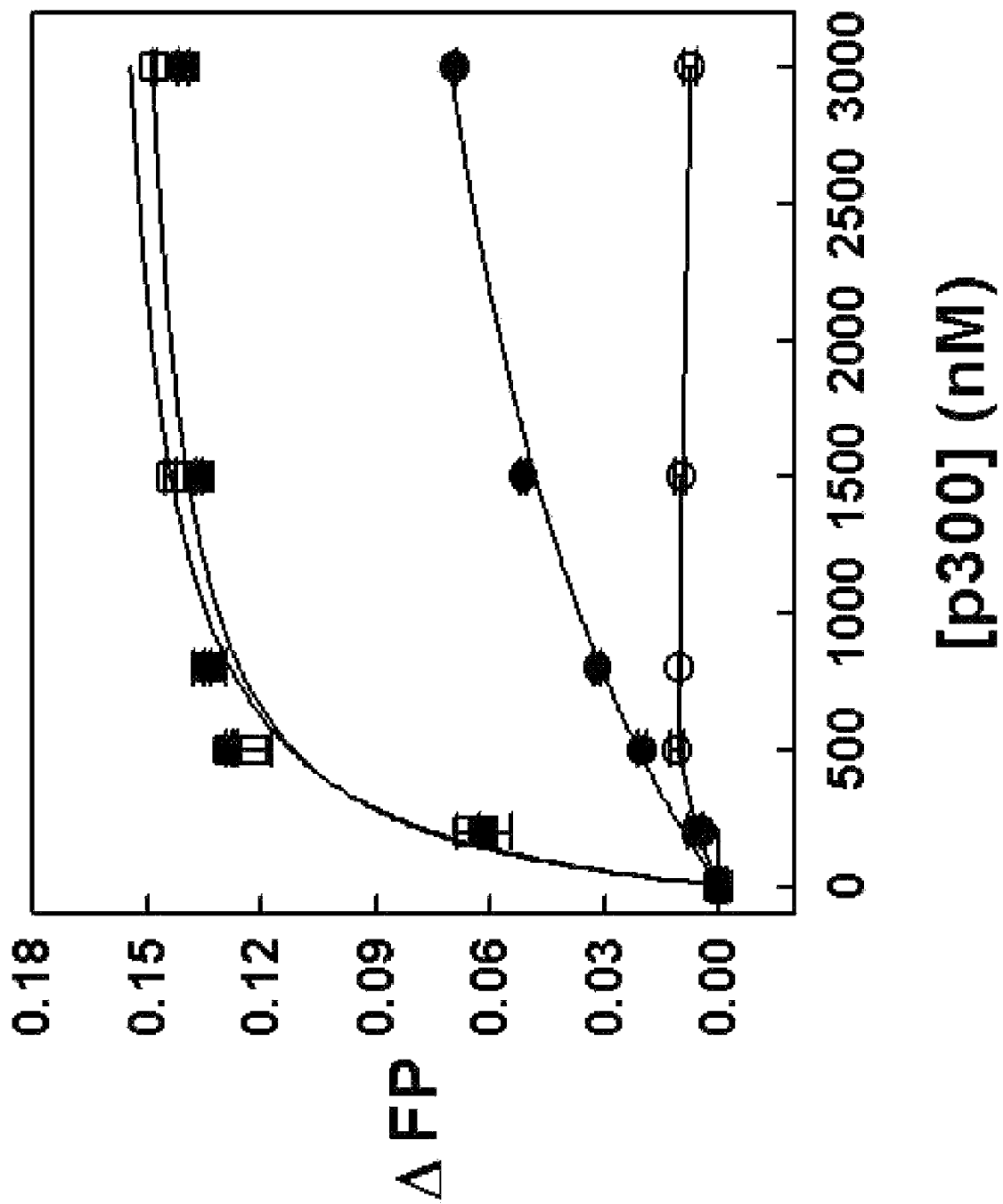

In the case of p300, FP values of HIF-1α(776-826, SEQ ID NO: 3) and HIF-1α(786-826, SEQ ID NO: 4) mixed with p300 similarly increased with increasing GST-p300 concentrations as shown in FIG. 2A (FIG. 2B). The dissociation constants of these two peptides were determined to be 157.3 nM for HIF-1α(776-826, SEQ ID NO: 3) and 180.1 nM for HIF-1α(786-826, SEQ ID NO: 4), respectively. On the other hand, FP values of HIF-1α(788-822, SEQ ID NO: 6) increased much less than those of the above two peptides, and the values of HIF-1α(776-814, SEQ ID NO: 5) showed no increase upon incubation with GST-p300 (FIG. 2B), indicating the critical role of the C-terminal helix of the HIF-1α C-TAD in p300 binding.

These results indicate that the simple FP-based measurements using fluorescein-labeled HIF-1α peptides enable quantitative evaluations of peptide fragments derived from the HIF-1α C-TAD for CBP or p300 binding activities.

Example 3

The Effects of Posttranslational Modifications (Hydroxylation, Nitrosation, and Phosphorylation) of HIF-1α on p300 Binding by Use of Fluorescence Polarization (FP)-Based Assay 3-1. Effect of Hydroxylation by FIH-1

Because hydroxylation on Asn-803 of HIF-1α prevents the HIF-1 transcriptional activation by inhibiting recruitment of CBP or p300 by HIF-1α (Lando, D., et al., Science, 295: 858-861, 2002), an embodiment of the present invention examined the direct hydroxylation effect of HIF-1α peptides on p300 binding by use of the FP-based assay. First, fluorescein-labeled HIF-1α peptides were treated with FIH-1 (Factor-inhibiting HIF-1) known as the enzyme that hydroxylates the specific asparagine residue of HIF-1α, and then the interaction of HIF-1α peptides with p300 was measured by use of the FP-based assay. The FIH-1 enzyme was separated and purified with the method as described below.

That is, the full-length human FIH-1 (amino acids 1-349; GenBank I.D.: AF395830) was subcloned in a pET-28 (Novagen) vector, and then overexpressed in E. coli BL21 (Novagen). The overexpressed FIH-1 proteins were purified, resuspended, and lysed according to the same method of CBP or p300 purification. The cell extracts were mixed with 2% TRITON X-100, left in ice for 10 min., and centrifuged at 13,000 rpm for 30 min. The supernatant was agitated on Ni-NTA agarose (Qiagen, USA) for 1 hour at 4° C., followed by washing twice with PBS, and the reaction mixtures were added to a Bio-Spin® Disposable Chromatography column (Bio-Red). Finally, His-FIH-1 proteins were eluted with 300 mM of imidazole solution, and then the purified fusion proteins were confirmed by SDS-PAGE and quantified by Bradford assay (Bio-Red).

For hydroxylation of the asparagine residue, 5 μM of F-HIF-1α (786-826, SEQ ID NO: 4) was incubated with 0.7 μg/μL of recombinant His-FIH-1 in hydroxylation reaction buffer (20 mM Tris-HCl, 5 mM KCl, 1.5 mM $MgCl_2$; pH 7.5) containing 400 μM Ascorbic acid and 100 μM α-ketoglutarate. After incubation for 2 hours at room temperature, the reaction mixtures were passed through $ZipTip_{C18}$ (Millipore, USA) for desalting, followed by elution from the tip by addition of α-cyano-4-hydroxycinnamic acid in acetonitrile/water containing 0.1% TFA (1:1 vol/vol). The eluted peptide solution was then transferred to a MALDI sample plate and MALDI-TOF measurements were performed with a Voyager analyzer (Applied Biosystems). For binding assays, the hydroxylated peptide was purified by reverse-phase HPLC.

To assess hydroxylation, MALDI-TOF analysis was first performed after F-HIF-1α (786-826, SEQ ID NO: 4) peptide was treated with recombinant His-FIH-1 protein, wherein the peptide contained the residues for p300 binding activity (FIG. 2B) as well as full FIH-1 activity. The results of hydroxylation of F-HIF-1α (786-826, SEQ ID NO: 4) by FIH-1 are depicted in FIG. 3A.

Figure 3A:
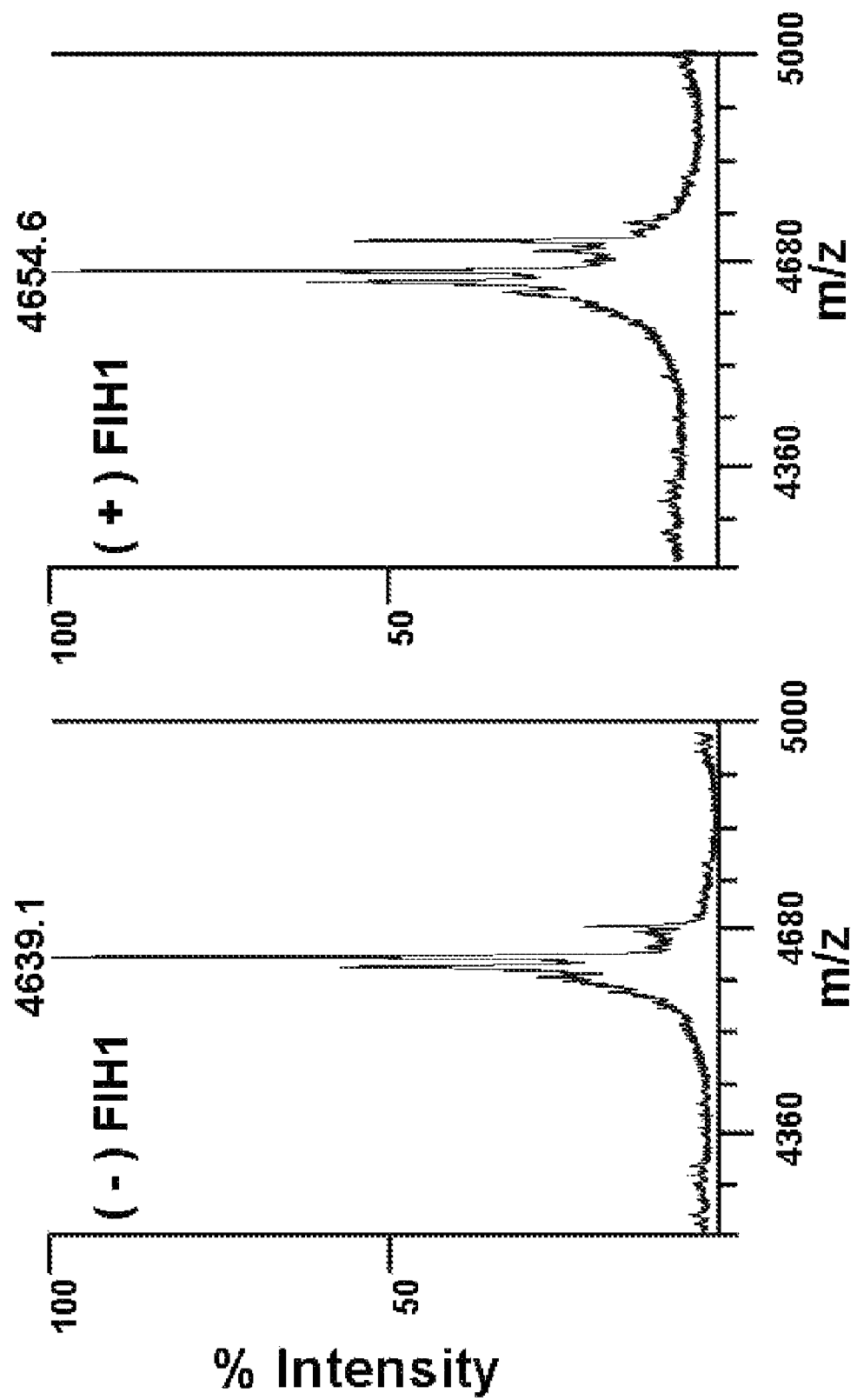
FIG. 3 is a graph showing the effects of asparagine hydroxylation of HIF-1α peptide on its binding to p300 protein, wherein FIG. 3A indicates the results of MALDI-TOF analysis for F-HIF-1α (786-826, SEQ ID NO: 4) peptides treated with or without FIH-1 (factor-inhibiting HIF-1) enzyme, and FIG. 3B indicates FP changes for the hydroxylated peptide (●) purified by reverse-phase HPLC after the reaction and untreated control peptide (○), respectively.

As shown in FIG. 3A, the peptide treated with His-FIH1 had an increase of mass of ~16 Daltons compared to the control (peptide treated without His-FIH-1) (FIG. 3A), indicating that the asparagine is hydroxylated by recombinant His-FIH-1. The hydroxylated F-HIF-1α (786-826, SEQ ID NO: 4) peptide was purified by reverse-phase HPLC and then used to monitor FP changes upon GST-p300 binding, since ascorbic acid and α-ketoglutarate included in the reaction mixtures could interfere with the HIF-1α-p300 interaction and FP measurements. The FP changes by the hydroxylated peptide were depicted in FIG. 3B.

Figure 3B:
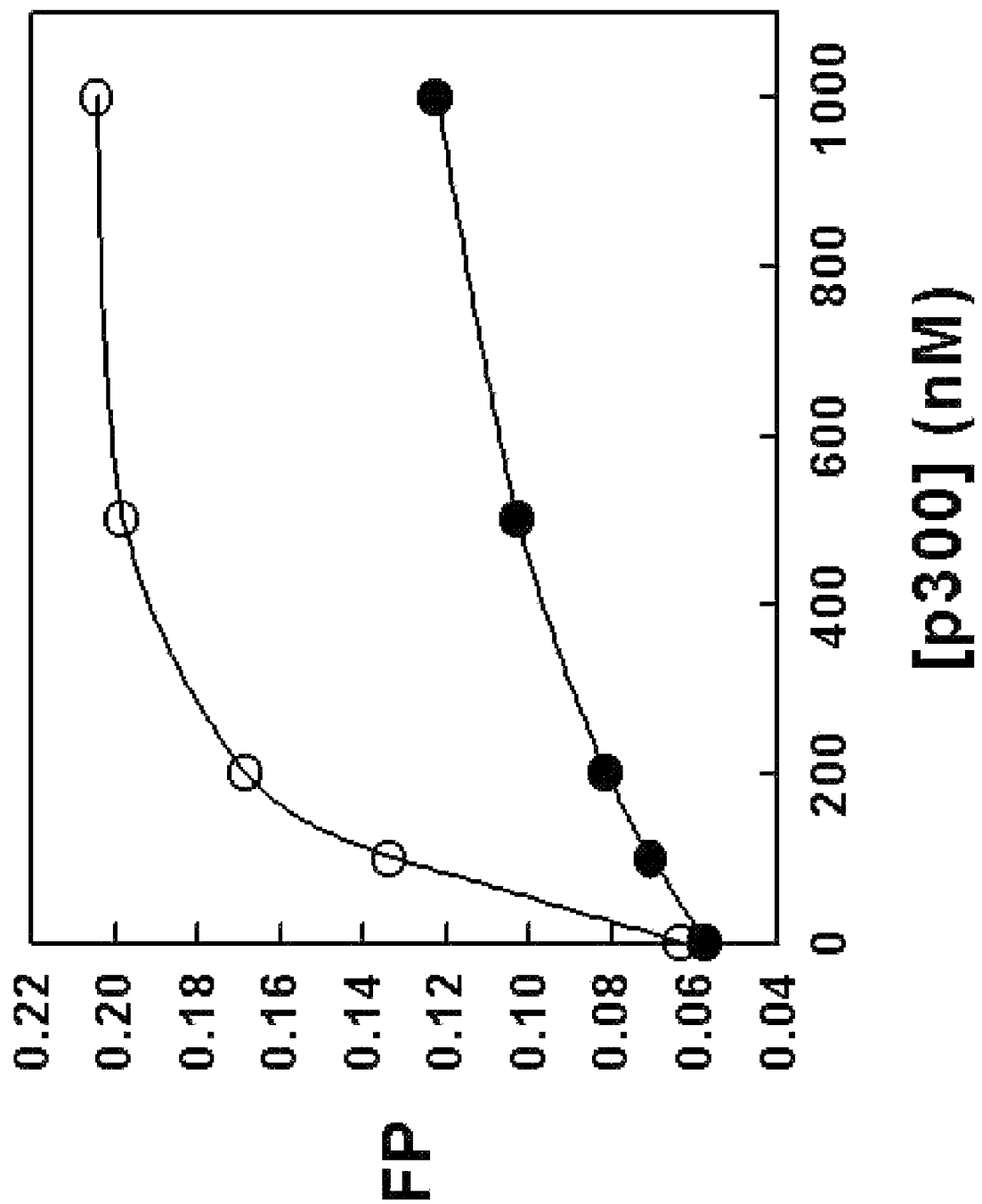

As shown in FIG. 3B, the degree of FP changes by the hydroxylated peptide only slightly increased with increasing p300 concentrations, but the degree of FP changes was much less than that of unmodified peptide (FIG. 3B). Therefore, these results indicated that asparagine hydroxylation of HIF-1α by FIH-1 could abrogate, although not fully, p300 binding activity.

3-2. Effect of S-Nitrosylation by SNAP

Figure 4A:
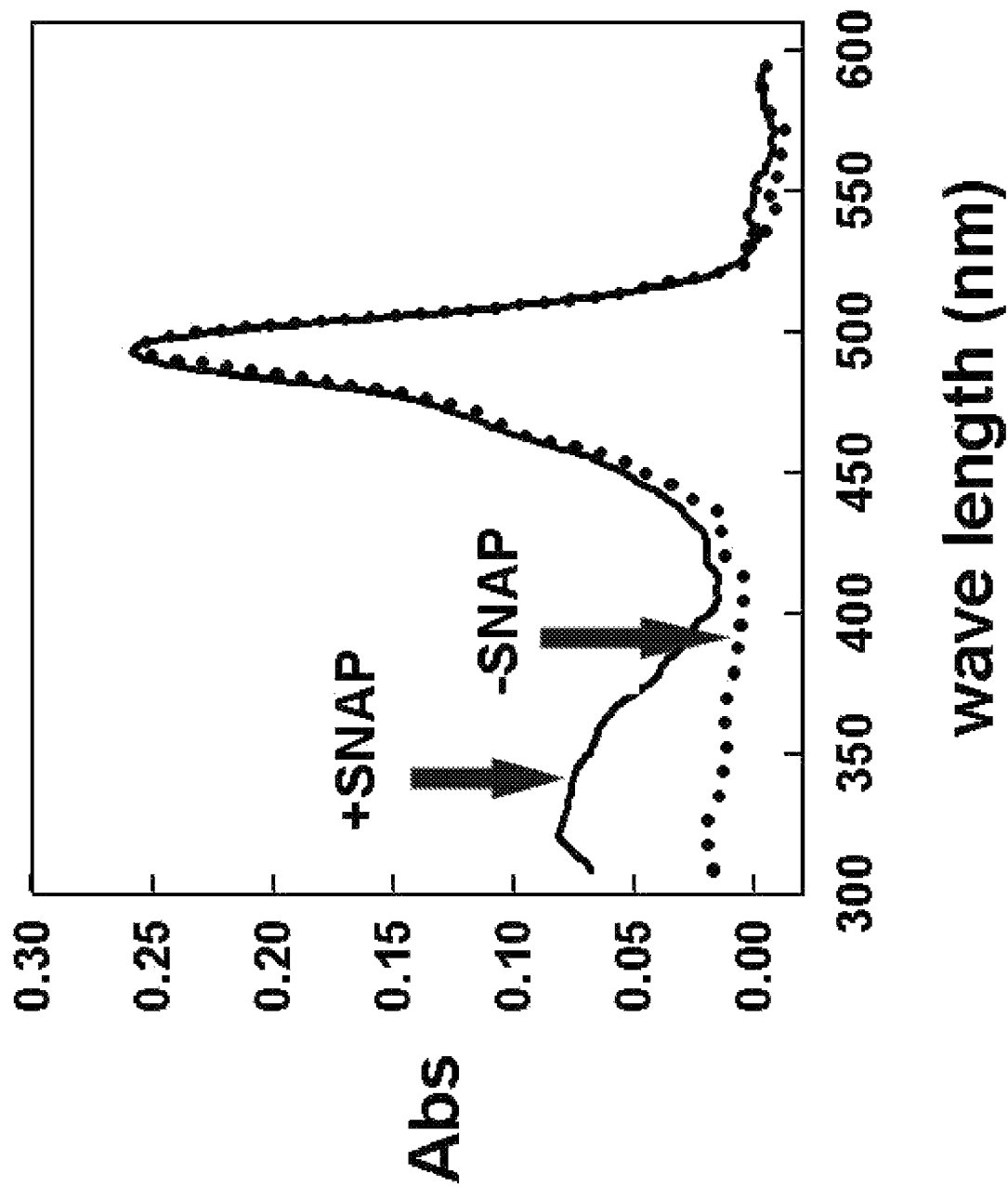
FIG. 4 is a graph showing the effects of S-nitrosylation of Cys-800 in HIF-1α peptide on its binding to p300 protein, wherein FIG. 4A indicates absorbance of the peptide treated with (solid line) or without SNAP (dotted line)
FIG. 4B indicates FP changes of wild-type (WT) and F-HIF-1α (786-826)[C800A] peptides containing Ala substitution for Cys pretreated with or without SNAP, wherein their peptides were incubated with or without a biotinylating reagent.
FIG. 4C indicates FP changes for (●), F-HIF-1α-(786-826, SEQ ID NO: 4); (■), S-nitrosylated F-HIF-1α (786-826, SEQ ID NO: 4); and (▲), F-HIF-1α (786-826)[C800A] peptides on its binding to p300, respectively.

S-nitrosylation on Cys-800 of HIF-1α has been reported to increase the p300 recruitment and its transcriptional activity, whereas nitric oxide (NO) has been shown to increase or decrease HIF-1α stability (Ema, M., et al., EMBO J., 18: 1905-1914, 1999; Yasinska, I. M. and Sumbayev, V. V., FEBS Lett., 549: 105-109, 2003; Hagen, T., et al., Science, 302: 1975-1978, 2003). According to an embodiment of the present invention, the effect of S-nitrosylation of Cys-800 in HIF-1α on its p300 binding was evaluated. Also, the nitrosothiol bond could not be detected by MDLDI-TOF analysis due to its photo-induced dissociation upon laser irradiation. Therefore, the formation of nitrosothiol bond was detected by the absorbance at ~320 nm, present in the SNAP-treated F-HIF-1α (786-826, SEQ ID NO: 4), but absent in the untreated peptide (FIG. 4A), wherein the peptide amounts were normalized to the fluorescein absorption peaks.

Additionally, the present invention was used to apply a biotinylation method for detecting and purifying S-nitrosylated peptides with a little modification of the previously reported method (Jaffery, S. R., et al., Na. Cell Biol., 3: 193-197, 2001). That is, F-HIF-1α (786-826, SEQ ID NO: 4) treated with or without S-nitroso-N-acetylpenicillamine (SNAP; Sigma-Aldrich) was reacted with the synthesized biotinylating reagent to biotinylate sulfhydryl groups. Because F-HIF-1α (786-826, SEQ ID NO: 4) has only one cysteine Cys-800, the modified peptide by S-nitrosylation cannot be biotinylated, whereas free cysteine in the untreated peptide is biotinylated. This biotinylation method allowed FP changes upon streptavidin addition, which also facilitated purification of the S-nitrosylated peptide, because S-nitrosylated and unmodified peptides were inseparable but S-nitrosylated and biotinylated peptides were readily separated by reverse-phase HPLC.

In detail, 30 μM of F-HIF-1α-(786-826, SEQ ID NO: 4) and F-HIF-1α (786-826)[C800A] containing Ala substituted for Cys were incubated with 2 mM SNAP in 50 mM Tris (pH 8.0) for 30 minutes at 30° C., respectively. After removing excess SNAP using a Sephadex G-15 resin, S-nitrosylation of the peptide was determined spectrophotometrically by measuring the absorbance of the nitrosothiol moiety (Jaffery, S. R., et al., Nat. Cell Biol., 3: 193-197, 2001). To confirm S-nitrosylation, 300 μM of the biotinylating reagent prepared as above was used to label unmodified cysteine after SNAP treatment. After incubation for 2 hours at room temperature, biotinylation was measured by changed FP upon streptavidin addition. Also, the S-nitrosylated peptide was obtained by separating it from the biotinylated one on reverse-phase HPLC for binding assays.

To prepare a biotinylating reagent for quantification of S-nitrosylation, biotin-Cys-NH$_2$ was first synthesized on Rink Amide™ resin (NovaBiochem) using 25 μmol of Fmoc-Cys according to a solid-phase peptide synthesis protocol. 12 mg of 1,11-bis-maleimidotriethyleneglycol (Pierce) was then added to the 1.5 ml solution of biotin-Cys-NH$_2$ (4 mg) in PBS/DMSO (1:2 vol/vol). After the mixture was stirred overnight at room temperature, the biotinylating reagent was purified by reverse-phase HPLC, and characterized by MALDI-TOF mass spectrometry. The FP values of the peptide treated with the biotinylating reagent were depicted in FIG. 4B.

Figure 4B:
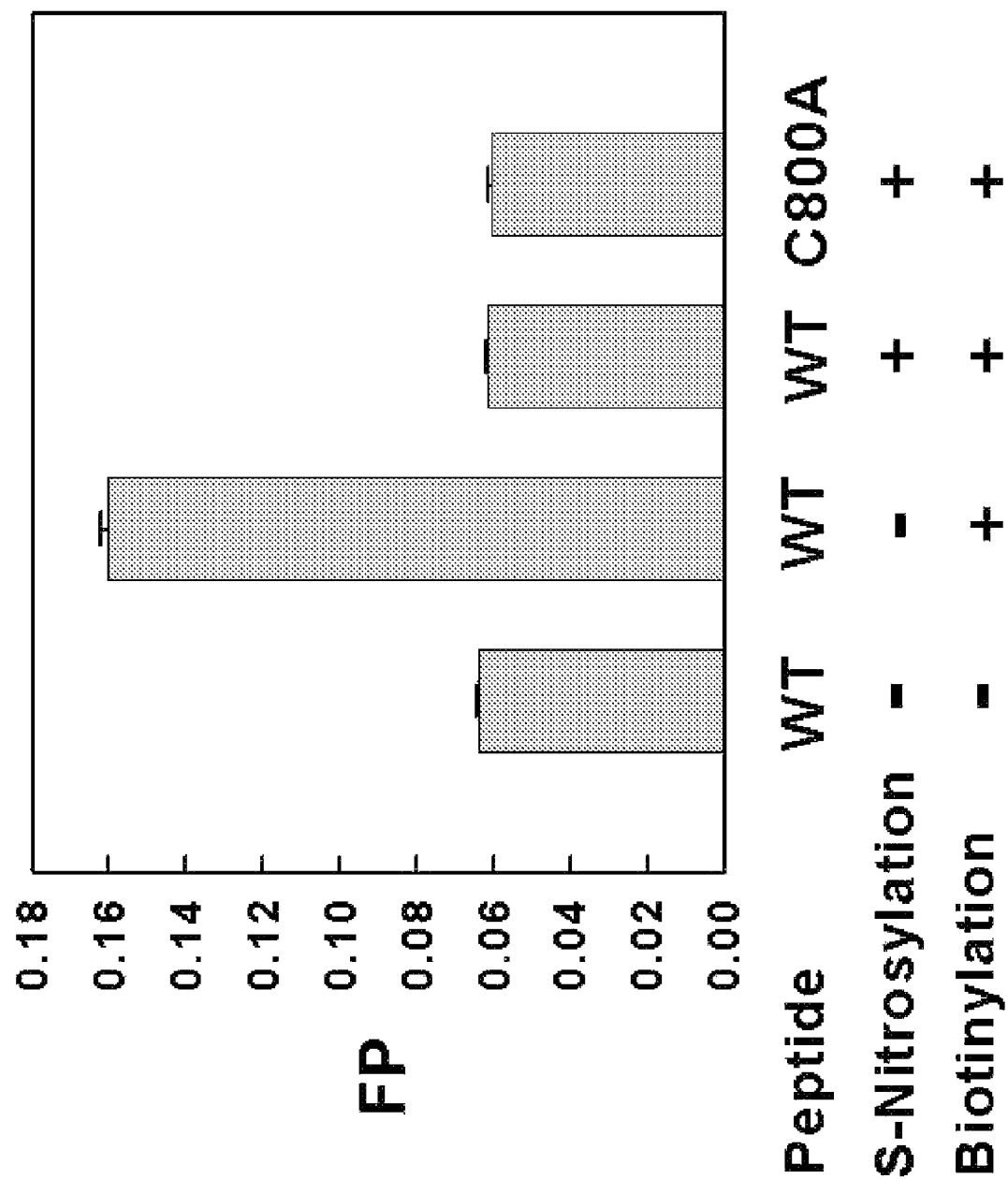

As shown in FIG. 4B, the addition of streptavidin increased FP values of the biotinylated peptide, but it did not change FP values of the S-nitrosylated peptide, since the S-nitrosylated peptides could not be biotinylated when treated with the biotinylating reagent. Moreover, when the mutant F-HIF-1α (786-826)[C800A]peptide, in which Cys-800 is converted to Ala, was treated with SNAP, followed by biotinylation, there was no change in the FP values (FIG. 4B).

Figure 4C:
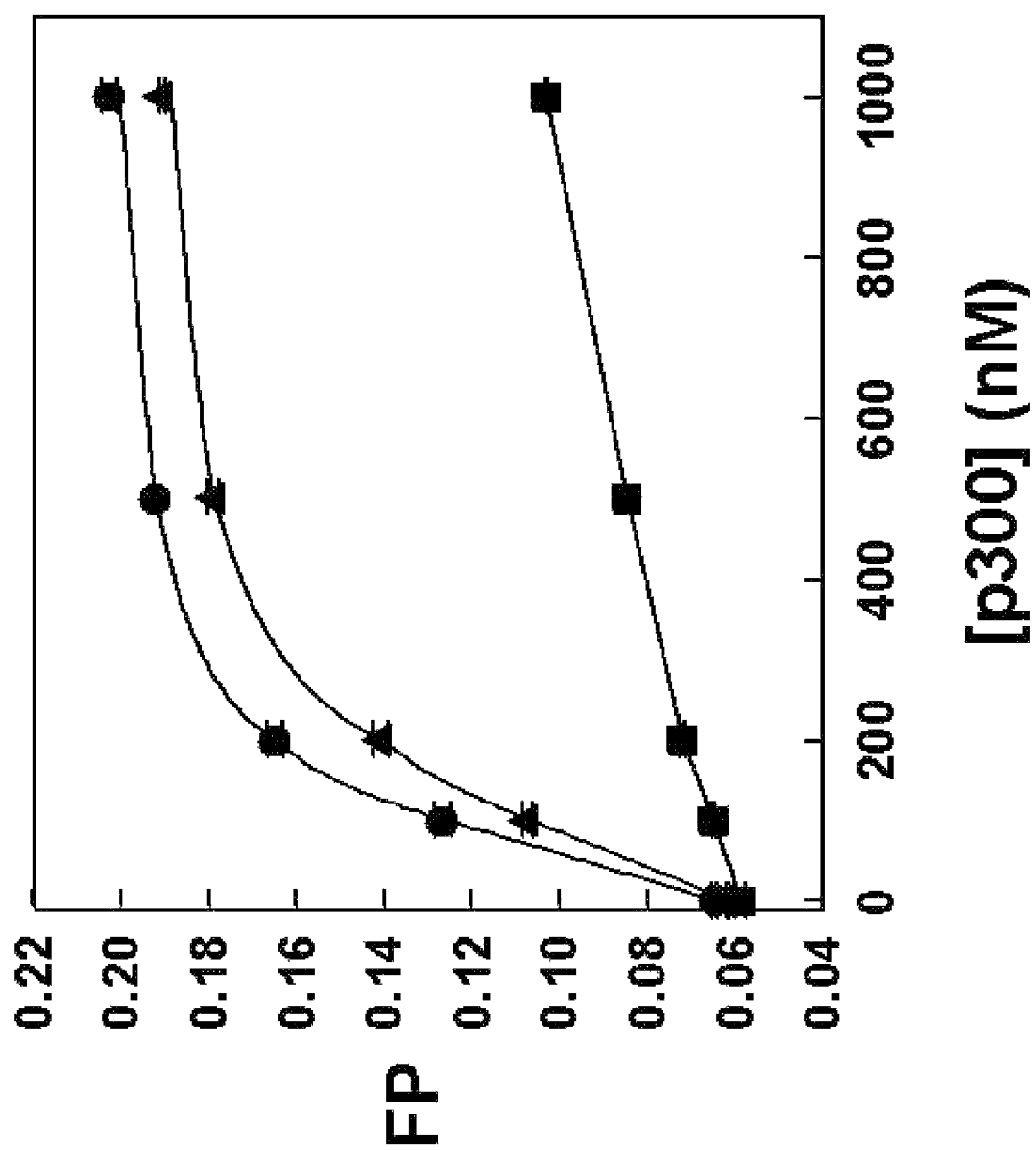

After S-nitrosylation of Cys-800 in F-HIF-1α (786-826, SEQ ID NO: 4) was confirmed, the effect on its p300 binding was analyzed. When S-nitrosylated, untreated F-HIF-1α (786-826, SEQ ID NO: 4), and F-HIF-1α (786-826)[C800A] mixed with GST-p300 were analyzed for FP, both F-HIF-1α (786-826)[C800A] and untreated F-HIF-1α (786-826, SEQ ID NO: 4) exhibited similar concentration-dependent binding patterns, while S-nitrosylated F-HIF-1α (786-826, SEQ ID NO: 4) showed only minimal increase in FP with increasing p300 concentrations (FIG. 4C).

These data indicate that S-nitrosylation of HIF-1α dramatically inhibits its p300 binding, which might work as a direct mechanism of decreased HIF-1α stability, although nitric oxide has been suggested to induce prolyl hydroxylase-dependent degradation of HIF-1α (Hagen, T., et al., Science, 302: 1975-1978, 2003).

3-3. Effect of Phosphorylation by Kinases

It has been reported that phosphorylation of Thr-796 in HIF-1α enhances the HIF-1α-CBP interaction (Gradin, K., et al., J. Biol. Chem., 277: 23508-23514, 2002), although phosphorylation sites of HIF-1α are far from the C-TAD (Mylonis, I., et al., J. Biol. Chem., 281: 33095-33106, 2006). Accordingly, an embodiment of the present invention evaluated the effect of phosphorylation of F-HIF-1α (786-826, SEQ ID NO: 4) on its p300 binding by use of a direct binding assay. Because protein kinases responsible for phosphorylating Thr-796 of HIF-1α have not yet been defined, kinase fractions obtained from the HeLa cells grown under hypoxia (H) and normoxia (N) were used to analyze phosphorylation of F-HIF-1α (786-826, SEQ ID NO: 4) on its binding to p300.

In detail, human HeLa cells cultured under normoxia (N) or hypoxia (H) conditions were collected, resuspended in a homogenization buffer (50 mM PIPES, 2 mM DTT, protease inhibitor cocktail, pH 7.0), and then lysed by sonication. To obtain the kinase fractions from the cell lysates, first cellulose phosphate resin (Whatman) swollen in 0.5 M of NaOH was poured into an open column with a sintered glass filter, until the filtrate pH became 3 with 0.5 M of HCl, followed by washing with 0.5 M of HEPES buffer at 4° C. Further, the cell lysates were loaded on the pre-equilibrated column with a washing buffer (0.5 M HEPES, 0.1 M NaCl, pH 7.5). After washing with the washing buffer to remove unbound materials, bound proteins were eluted with an elution buffer (0.5 M HEPES, 0.45 M NaCl, pH 7.5), followed by quantification using the Bradford method.

For phosphorylation, reactions were carried out with normoxic or hypoxic kinases (40 μg), or CK2 (500 units; New England Biolabs, Beverly, USA) in 50 μL of kinase reaction buffer (25 mM HEPES, 20 mM MgCl$_2$, 2 mM DTT, 0.1 mM Na$_3$VO$_4$, pH 7.5) with 100 μM of ATP with or without [γ-$^{32}$P] ATP using 3 μM of F-HIF1α-(786-826, SEQ ID NO: 4) as substrates. For binding assays, the phosphorylated product was purified by reverse-phase HPLC after reacting without [γ-$^{32}$P]ATP overnight at room temperature. The results of phosphorylation of the F-HIF-1α (786-826, SEQ ID NO: 4) peptide by normoxic (N) or hypoxic (H) kinase fractions are depicted in FIG. 5A.

Figure 5A:
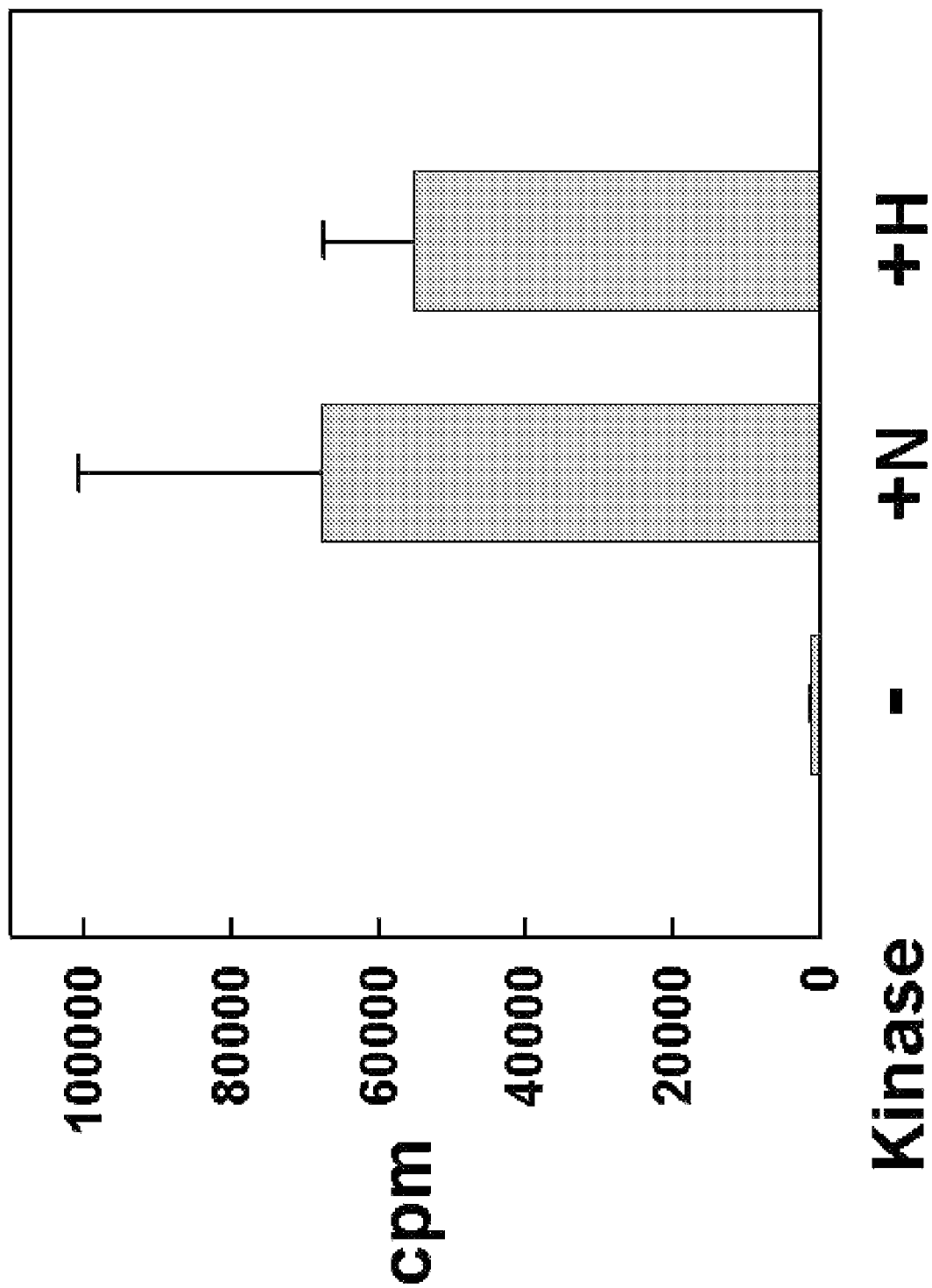
FIG. 5 is a graph showing the effects of phosphorylation of HIF-1α peptide on its binding to p300 protein, wherein FIG.
FIG. 5B indicates the binding activity of its peptide treated with or without p300 protein.
FIG. 5C indicates the level of phosphorylation of HIF-1α peptide by CK2.
FIG. 5D indicates the binding activity of untreated (●) or phosphorylated (○) HIF-1α peptides, wherein the binding activity in FIGS. 5B and 5D was measured by FP analysis, and the level of phosphorylation in FIGS. 5A and 5C was measured by radioactive analysis, respectively.

As shown in FIG. 5A, the radioactivity of the peptide treated with normoxic (N) or hypoxic (H) kinase fractions dramatically increased compared to that of the control (peptide treated without kinase) (FIG. 5A).

Figure 5B:
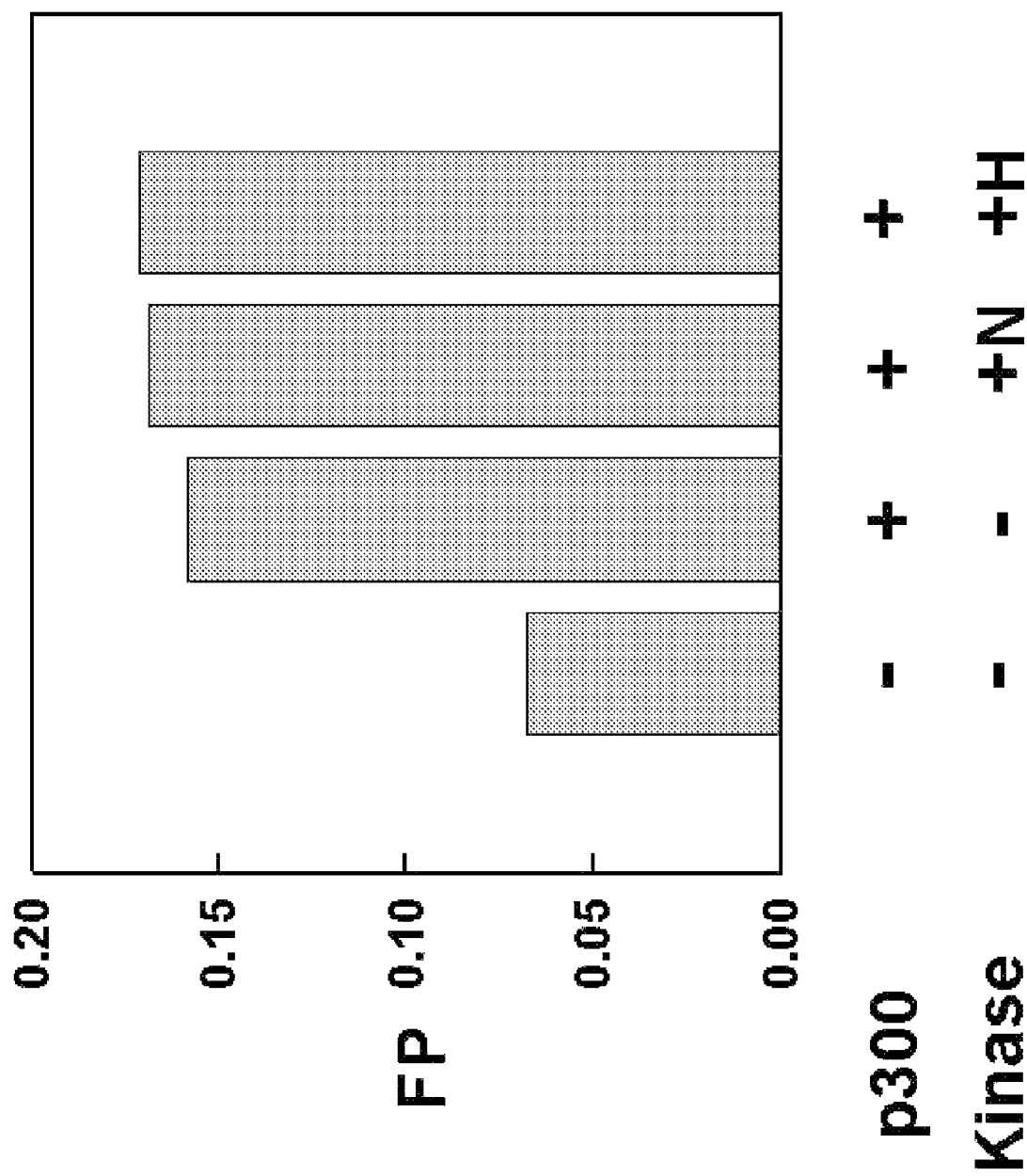
Figure 5C:
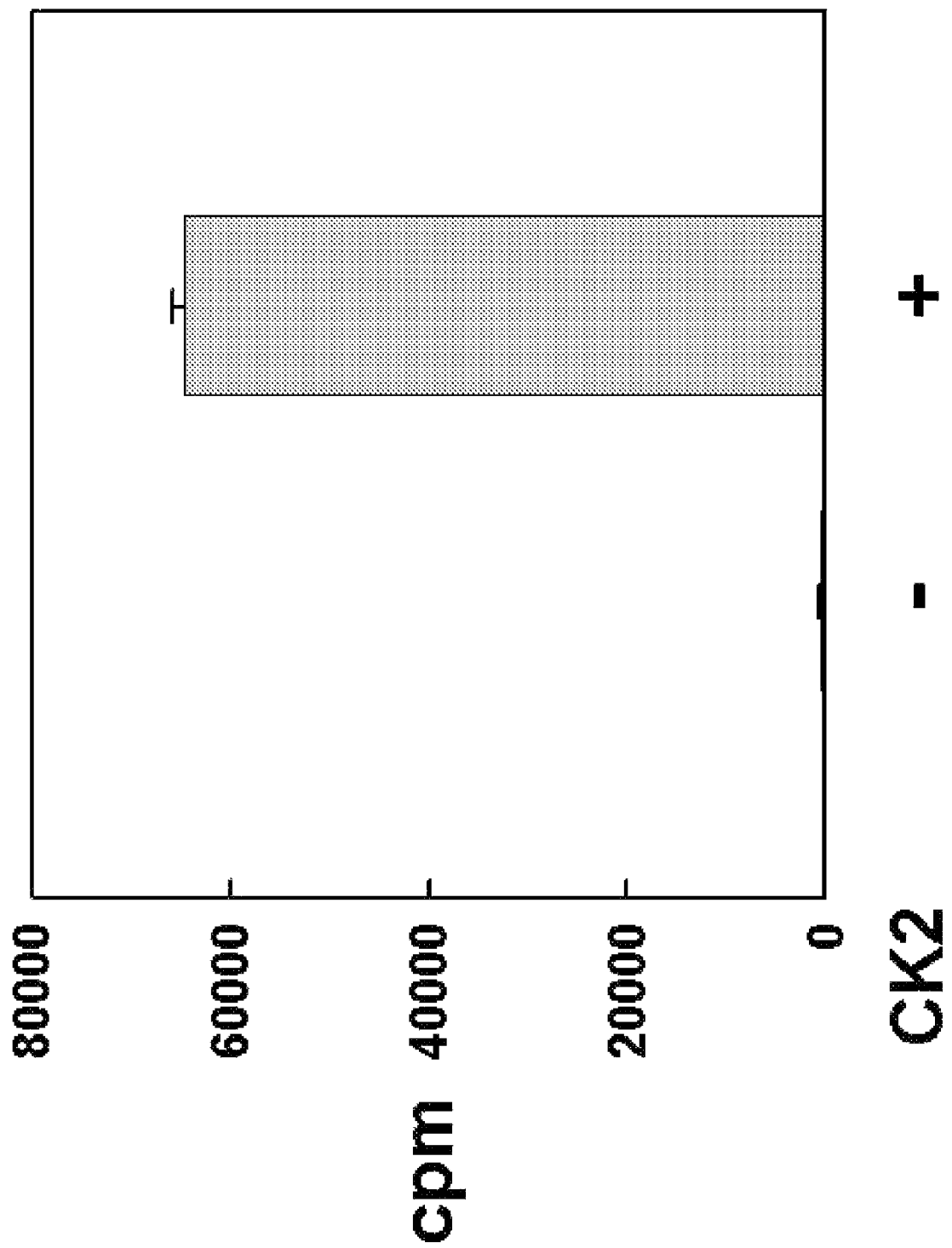
Figure 5D:
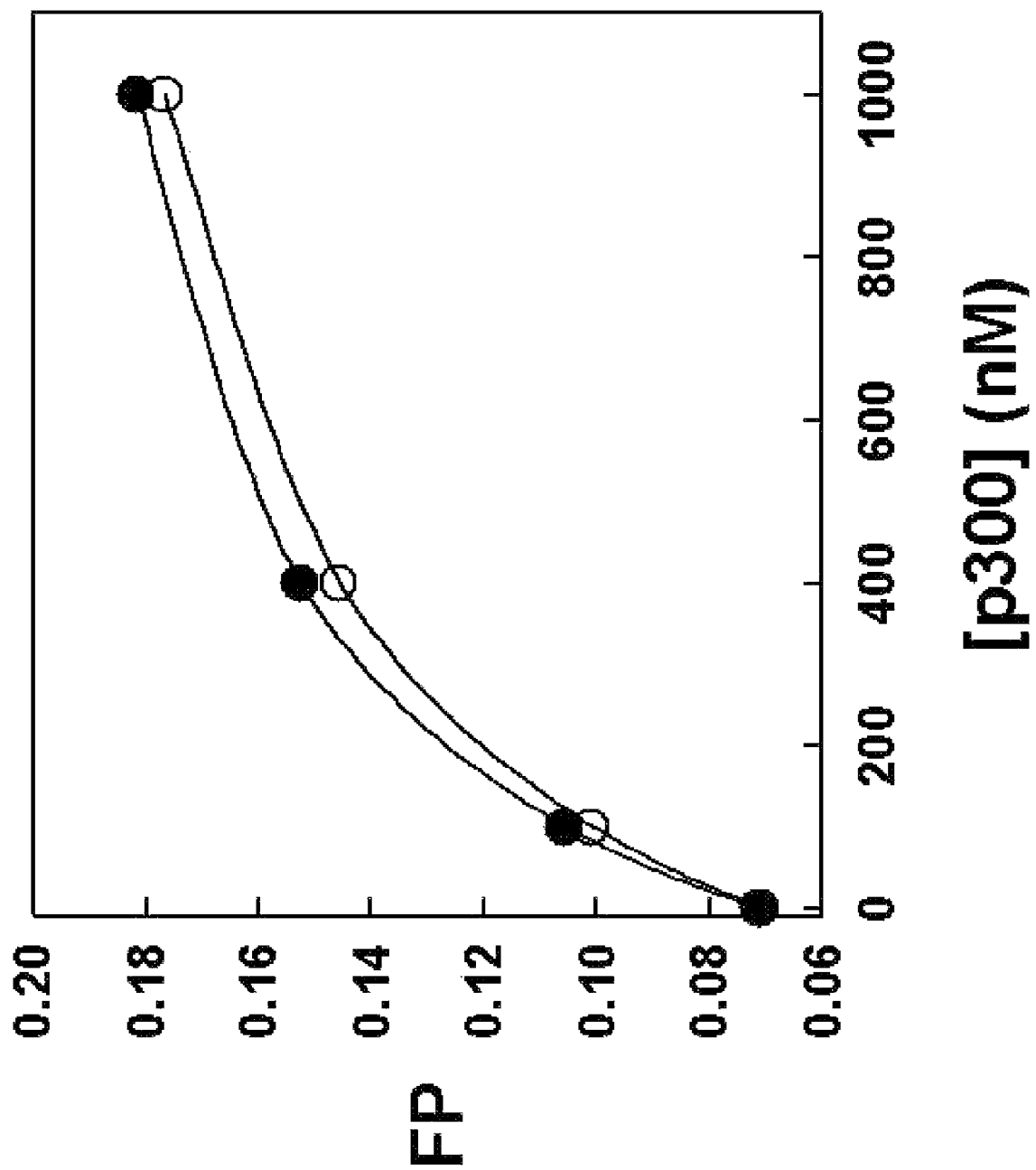

Also, the peptide treated with N or H kinase fractions and purified by reverse-phase HPLC showed an FP increase upon incubation with GST-p300, similar to the untreated peptide (FIG. 5B). In addition, since Thr-796 present in the peptide is a putative CK2 phosphorylation site (Mottet, D., et al., Int. J. Cancer, 117: 764-774, 2005), the F-HIF-1α-(786-826, SEQ ID NO: 4) peptide was phosphorylated by CK2 (FIG. 5C). The FP of the purified CK2-phosphorylated peptide showed a similar p300 binding pattern compared to that of the untreated peptide (FIG. 5D).

Therefore, these results indicated that phosphorylation of C-TAD in HIF-1α unlikely affects the HIF-1α-p300 interaction, and the increased transcriptional activity upon phosphorylation may involve other mechanisms (Brahimi-Horn, C., et al., Cell. Signal., 17: 1-9, 2005).

3-4. Competitive Binding Analysis

To compare the importance of Thr-796, Cys-800, and Asn-803 residues in the HIF-1α peptide on its p300 binding activity, an embodiment of the present invention performed competitive inhibition analyses of the FP-based binding assays using single mutant peptides. The mutant peptides were prepared with the method as described below.

Namely, human HIF-1α-(786-826, SEQ ID NO: 4) and its single mutation products prepared by PCR were subcloned into pGEX-2T-1 (Amersham Biosciences), and overexpressed in *E. coli* BL21 (DE3). After the GST fusion proteins were purified using glutathione-SEPHAROSE (Amersham Biosciences), followed by GST removal with thrombin treatment, the resulting peptides were purified using reverse-phase HPLC and confirmed by MALDI-TOF mass spectrometry. The results of competitive inhibition for HIF-1α-(786-826, SEQ ID NO: 4) peptides with point mutations on the HIF-1α-p300 interaction are depicted in FIG. 6.

Figure 6:
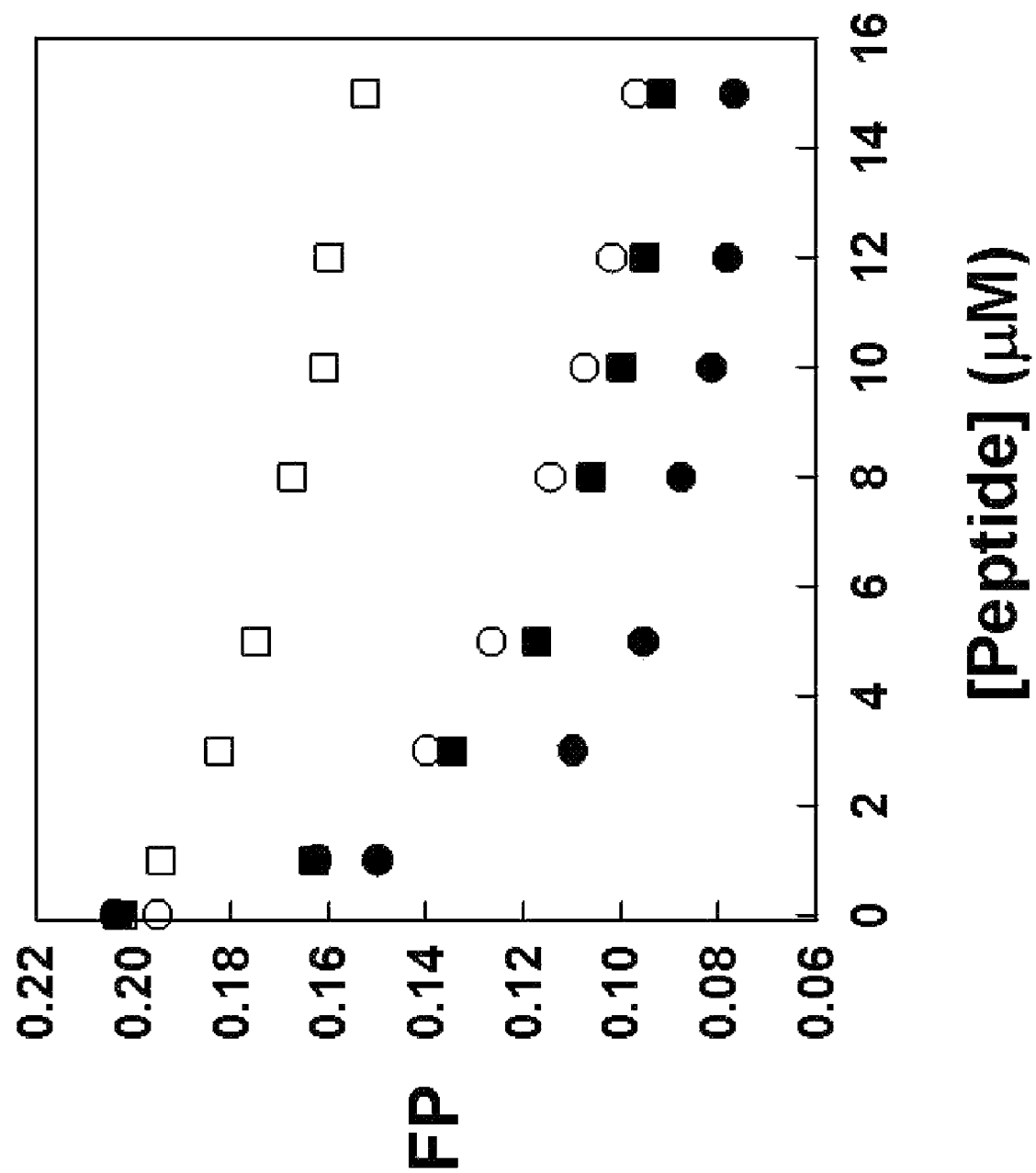
FIG. 6 is a graph showing competitive inhibition ability for F-HIF-1α peptides with point mutations on the F-HIF-1α-p300 interaction, wherein (●), (■), (○), and (□) indicate wild-type, T796D, N803A, and C800S HIF-1α (786-826) peptides, respectively.

As shown in FIG. 6, in the FP for the mixtures of GST-p300 and F-HIF-1α-(786-826, SEQ ID NO: 4) containing varying concentrations of wild-type and single mutant peptides, the wild-type peptide with 786-826 residues of HIF-1α effectively competed with F-HIF-1α-(786-826, SEQ ID NO: 4) for the p300 binding ($K_i$ of 318.6 nM), but the C800S mutant peptide was a poor inhibitor ($K_i$ of 3592.3 nM) (FIG. 6). These results were consistent with the previous report that hydrophilic substitutions of Cys-800 in HIF-1α with Ser or Asp disturb p300 binding, but hydrophobic substitutions with Ala or Val do not (Gu, J., et al., J. Biol. Chem., 276: 3550-3554, 2001), which was also shown by the p300 binding results using F-HIF-1α (786-826)[C800A] (FIG. 4C).

On the other hand, T796D and N803A mutant peptides competitively inhibited F-HIF-1α-(786-826, SEQ ID NO: 4) on its binding to p300 to a little lesser degrees than the wild-type (FIG. 6). These results indicated that mutation of Asn-803 to Ala has little effects in p300 binding but abolishes hydroxylation by FIH-1 (data not shown), and also confirmed that phosphorylation of Thr-796 does not play a significant role at least in p300 binding.

In conclusion, the results presented herein could resolve some conflicting issues of the effects of posttranslational modifications on p300 binding activity, although such effects might be exerted to HIF-1α-mediated transcription via some other mechanisms rather than direct modulations of the HIF-1α-p300 binding.

It is to be understood that the above-described embodiments are only illustrative of the applications of the principles of the present invention. Numerous modifications and alternative embodiments can be derived without departing from the spirit and scope of the present invention, and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

What is claimed is:

1. A method for quantitative analysis of an interaction between HIF-1α and cAMP-responsive element binding protein (CBP) or p300 protein, which comprises the steps of:
   1) preparing a fluorescent probe by attaching a fluorescein to peptides derived from the C-terminal transactivation domain of HIF-1α protein having at least 41 but no more than 55 amino acids which are consecutively presented in the full-length amino acid sequence;
   2) reacting the fluorescent probe with CBP or p300 proteins wherein the reaction is induced by mixing the fluorescent probe with CBP or p300 protein within ranges from 1:2 to 1:10; and
   3) measuring fluorescence polarization (FP) values for the reaction mixture obtained in step 2) and then comparing with that of the fluorescent probe itself to analyze the changes of FP values.

2. The method for quantitative analysis according to claim 1, wherein the peptide essentially comprises the amino acid sequence through the 786$^{th}$ amino acid to the 826$^{th}$ amino acid in HIF-1α shown in SEQ ID NO: 4;
   an aminocaproic acid linker conjugated to the N-terminus of the peptide; and
   a fluorophore linked at the end of aminocaproic acid.

3. The method for quantitative analysis according to claim 2, wherein the fluorescent probe comprises the peptide having amino acid sequences shown in SEQ ID NO: 3.

4. The method for quantitative analysis according to claim 1, wherein the CBP comprises amino acid sequences shown in SEQ ID NO: 1.

5. The method for quantitative analysis according to claim 1, wherein the p300 protein comprises amino acid sequences shown in SEQ ID NO: 2.

6. The method for quantitative analysis according to claim 1, wherein a fluorophore containing fluorescein is selected from the group consisting of fluorescein isothiocyanate (FITC), phycoerythrin (PE), Texas Red (TR) and tetramethylrhodamine isothiocyanate (TRITC), fluorescein carboxylic acid (FCA), fluorescein thiourea (FTH), 7-acethocycoumarin-3-1, fluorescein-5-1, fluorescein-6-1, 2',7'-dichlorofluorescein-5-1, dehydrotetramethylosamine-4-1, tetramethylrhodamine-5-1, and tetramethylrhodamine-6-1.

7. The method for quantitative analysis according to claim 1, wherein the reaction is induced by mixing a fluorescent probe with CBP or p300 proteins within ranges from 100 nM: 200 nM to 100 nM: 1000 nM.

8. A method of screening inhibitors against an interaction between HIF-1α and CBP or p300 proteins, which comprises the steps of:
   1) adding an inhibitor candidate to a reaction solution containing a fluorescent probe and CBP or p300 protein, wherein the fluorescent probe is prepared by attaching a fluorescein to peptides derived from the C-terminal transactivation domain of HIF-1α protein having at least 41 but no more than 55 amino acids which are consecutively presented in the full-length amino acid sequence, and the fluorescent probe and CBP or p300 protein are mixed within ranges from 1:2 to 1:10;
   2) measuring the change of fluorescence polarization (FP) values of the reaction solution before and after addition of the inhibitor candidate; and
   3) determining the candidate as an inhibitor by detecting a decrease in FP values of the reaction solution after addition of the inhibitor candidate.

9. The method of screening inhibitors according to claim 8, wherein the peptide essentially comprises the amino acid sequence through the 786$^{th}$ amino acid to the 826$^{th}$ amino acid in HIF-1α shown in SEQ ID NO: 4;
   an aminocaproic acid linker conjugated to the N-terminus of the peptide; and
   a fluorophore linked at the end of aminocaproic acid.

10. The method of screening inhibitors according to claim 9, wherein the fluorescent probe comprises the peptide having amino acid sequences shown in SEQ ID NO: 3.

11. The method of screening inhibitors according to claim 8, wherein the CBP comprises amino acid sequence shown in SEQ ID NO: 1.

12. The method of screening inhibitors according to claim 8, wherein the p300 protein comprises amino acid sequences shown in SEQ ID NO: 2.

13. The method according to claim 1, wherein the method comprises the steps of:
   a) preparing a fluorescent probe by attaching a fluorescein to a C-terminal transactivation domain of HIF-1α protein having at least 41 but no more than 55 amino acids which are consecutively presented in the full-length amino acid sequence; reacting the fluorescent probe with CBP or p300 protein wherein the reaction is induced by mixing the fluorescent probe with CBP or p300 protein within ranges from 1:2 to 1:10, and then measuring FP values thereof;

b) treating the fluorescent probe with an enzyme selected from the group consisting of Factor-inhibiting HIF-1 (FIH-1), S-Nitroso-N-acetylpenicillamine (SNAP), and casein kinase 2 (CK2), reacting the enzyme-treated probe with CBP or p300 protein, and then measuring FP values thereof; and c) comparing the FP values measured in step a) and step b) to analyze the effect of the posttranslational modifications of the C-terminal transactivation domain (C-TAD) of the HIF-1α on CBP or p300 binding.

* * * * *